United States Patent
Kohlhase et al.

(10) Patent No.: US 7,820,150 B2
(45) Date of Patent: *Oct. 26, 2010

(54) COSMETIC OR DERMATOLOGICAL FORMULATIONS OF IMPROVED PEARLESCENCE

(75) Inventors: Silke Kohlhase, Hamburg (DE); Andreas Bleckmann, Ahrensburg (DE); Heidi Riedel, Hamburg (DE); Stefanie Von Thaden, Hamburg (DE)

(73) Assignee: Beiersdorf AG, Hamburg (DE)

( * ) Notice: Subject to any disclaimer, the term of this patent is extended or adjusted under 35 U.S.C. 154(b) by 1385 days.

This patent is subject to a terminal disclaimer.

(21) Appl. No.: 10/759,254

(22) Filed: Jan. 20, 2004

(65) Prior Publication Data

US 2004/0228888 A1 Nov. 18, 2004

(30) Foreign Application Priority Data

Jan. 20, 2003 (DE) .................................. 103 01 834

(51) Int. Cl.
C11D 1/62 (2006.01)
A61K 8/73 (2006.01)
A61K 8/02 (2006.01)

(52) U.S. Cl. .................. 424/70.28; 424/70.13; 424/401

(58) Field of Classification Search .............. 424/70.28, 424/70.13, 401
See application file for complete search history.

(56) References Cited

U.S. PATENT DOCUMENTS

| | | | |
|---|---|---|---|
| 4,370,319 A * | 1/1983 | Chapin et al. ................. | 514/63 |
| 4,742,142 A | 5/1988 | Shimizu et al. | |
| 4,761,454 A | 8/1988 | Oba et al. | |
| 4,870,167 A | 9/1989 | Zody et al. | |
| 4,980,167 A | 12/1990 | Harashima et al. | |
| 5,266,321 A | 11/1993 | Shukuzaki et al. | |
| 5,334,387 A | 8/1994 | Haugk | |
| 5,346,691 A | 9/1994 | Raspanti | |
| 5,403,944 A | 4/1995 | Frater et al. | |
| 5,426,182 A | 6/1995 | Jenkins et al. | |
| 5,654,362 A | 8/1997 | Schulz, Jr. et al. | |
| 5,880,076 A * | 3/1999 | Vermeer ..................... | 510/123 |
| 5,955,060 A | 9/1999 | Hüglin et al. | |
| 6,251,954 B1 | 6/2001 | Roulier et al. | |
| 6,486,106 B1 | 11/2002 | Charlton et al. | |
| 6,558,680 B1 * | 5/2003 | Riedel et al. ................. | 424/401 |
| 2002/0197213 A1 | 12/2002 | Schmenger et al. | |
| 2003/0224025 A1 | 12/2003 | Gotsche et al. | |
| 2004/0057915 A1 | 3/2004 | Gers-Barlag et al. | |
| 2004/0241105 A1 | 12/2004 | Riedel et al. | |

FOREIGN PATENT DOCUMENTS

| | | |
|---|---|---|
| DE | 4344661 | 6/1995 |
| DE | 69111466 | 4/1996 |
| DE | 19933466 | 1/2000 |
| DE | 19921186 | 11/2000 |
| DE | 19942714 | 3/2001 |
| DE | 19943436 | 3/2001 |
| DE | 19944545 | 3/2001 |
| DE | 19950059 | 4/2001 |
| DE | 10041220 | 3/2002 |
| EP | 0281360 | 9/1988 |
| EP | 0295886 | 12/1988 |
| EP | 0570838 | 11/1993 |
| EP | 0612518 | 8/1994 |
| EP | 0775698 | 5/1997 |
| EP | 1046387 | 10/2000 |
| EP | 1295589 | 3/2003 |
| EP | 1352641 | 10/2003 |
| JP | 2-243612 | 9/1990 |
| WO | 90/10429 | 9/1990 |
| WO | 92/09264 | 6/1992 |
| WO | 92/20690 | 11/1992 |
| WO | 00/69404 | 11/2000 |
| WO | 01/10403 | 2/2001 |
| WO | 01/52800 | 7/2001 |
| WO | 02/05769 | 1/2002 |
| WO | 02/074258 | 9/2002 |
| WO | 02/074264 | 9/2002 |
| WO | 03/022238 | 3/2003 |

OTHER PUBLICATIONS

English Language Abstract of DE 199 50 059.
English Language Abstract of DE 199 42 714.
English Language Abstract of DE 199 21 186.
English Language Abstract of DE 199 44 545.
English Language Abstract of DE 43 44 661.
English Language Abstract of DE 199 43 436.
Modern Cosmeticology, vol. 1, 1996, Ralph G. Harry, F.R.I.C., 1962, pp. 115-119.
Kosmetologie, 3$^{rd}$ edition, 1976, Dr. J. Jellinek (pp. 235-239).
English Language Abstract of EP 1295589.
English Language Abstract of EP 1352641.
English Language Abstract of DE 19933466.

* cited by examiner

*Primary Examiner*—Kevin Weddington
(74) *Attorney, Agent, or Firm*—Greenblum & Bernstein, P.L.C.

(57) ABSTRACT

A cosmetic or dermatological preparation which comprises a $C_{12}$-$C_{40}$ fatty acid, a $C_{12}$-$C_{40}$ fatty alcohol, an amphiphilic polymer, an associative polymer and/or a siloxane elastomer, sodium and/or potassium hydroxide, and a pigment and/or a dye.

60 Claims, No Drawings

COSMETIC OR DERMATOLOGICAL FORMULATIONS OF IMPROVED PEARLESCENCE

BACKGROUND OF THE INVENTION

1. Field of the Invention

The invention relates to cosmetic preparations with a pearlescent effect and good skin compatibility, and to the use thereof.

2. Discussion of Background Information

Customary cosmetic application forms and preparations are often emulsions. This term is generally understood as meaning a heterogeneous system of two liquids which are immiscible or miscible only to a limited extent with one another and are usually referred to as phases. One is in the form of droplets (disperse or internal phase), whilst the other liquid forms a continuous (coherent or internal) phase. Less common application forms are multiple emulsions, i.e. those which, in the droplets of the dispersed (or discontinuous) phase, comprise for their part droplets of a further dispersed phase, e.g. W/O/W emulsions and O/W/O emulsions.

More recent findings have recently led to a better understanding of cosmetic emulsions which are of relevance in practice. Here, it is assumed that the emulsifier mixtures used in excess form lamellar liquid-crystalline phases or crystalline gel phases. In the gel network theory, stability and physicochemical properties of such emulsions are attributed to the formation of viscoelastic gel networks. In order to be able to ensure the metastability of emulsions, interface-active substances, i.e. emulsifiers, are usually necessary.

Emulsions from the prior art have a pearlescent effect, as is described, for example, in WO 0110403, WO 9010429, DE 19921186 or DE 19944545. These cosmetic preparations comprise mono- and di-fatty acid esters of glycerol or glycol, such as, for example glycerol stearates, laurates or myristates, in order to ensure pearlescence of the preparation. These fatty acid esters form lamellar structures with lyotropic, liquid-crystalline properties arranged in O/W emulsions. This leads to an optical property of the emulsions comprising them which is referred to as pearlescence.

Preparations with pearlescence optics without the addition of these fatty acid esters are not accessible or accessible only with difficulty.

Cosmetic preparations and emulsions with pearlescence optics based on the emulsifier "stearic acid/palmitic acid" have been known for a long time. It was hitherto not possible to formulate pearlescent emulsions which have the neutralizing agent NaOH and fractions of fatty acids below 12% by weight.

In view of this, the pearlescent emulsions known from the prior art and available commercially exhibit very poor skin compatibility.

An optical pearlescent effect is achieved in cosmetic preparations according to the prior art exclusively by neutralization with triethanolamine or potassium hydroxide solution. With sodium hydroxide solution, no systems with mother of pearl-like optics could hitherto be prepared, as detailed, for example, in Modern Cosmeticology, Volume one, 1996, Ralph G. Harry, F. R. I. C, 1962, pp. 115-119. It is likewise clear in this that lipids and waxes inhibit the pearlescence in emulsions. Pearlescent emulsions are described which comprise very small, up to a maximum of 3% by weight, fractions of lipids and/or lipophilic consistency-imparting agents.

In addition, it is known that the sole use of sodium hydroxide solution in these systems does not ensure adequate storage stability of the cosmetic preparation, as explained, for example, in The American Perfumer, April 1945, "Manufacturing Vanishing Cream", J. S. Shukla. This also discloses that pearlescent emulsions can be achieved exclusively by means of high use concentrations of fatty acids. Thus, for example, 16-25% by weight of fatty acids, where 13.3% by weight should be hydrolysed, are used. However, it is also known, for example from Kosmetologie, 3rd edition, 1976, Dr. J. Jellinek (pp. 235-239), that precisely this high soap content of 13.3% by weight leads to poor skin compatibilities.

Cosmetic preparations with pearlescent effects have visible effects in the product, although these are no longer visible on the skin or are different from the subsequent appearance on the skin.

It is therefore customary to add pigments or dyes to the preparations in order to enhance the effect on the skin. A disadvantage of preparations to date with pigment additives without pearlescent effects is that the preparations have no shimmer effect within the product. The disadvantage associated with this is that although preparations to which pigments have been added have a shimmer effect on the skin, they do not have a shimmer effect within the product. The user can in no way discern the optical effect to be achieved on the skin by reference to the product.

An object of the present invention is to provide a cosmetic preparation which has an optically pleasing effect, in particular a pearlescent effect, adequate storage stability and, in particular, good skin compatibility. In particular, the object of the present invention is to provide a preparation with pearlescent effects which offers this effect both on the skin and also within the product.

Moreover, the object of the present invention is to provide a cosmetic preparation which enriches the prior art.

SUMMARY OF THE INVENTION

The present invention provides a first cosmetic or dermatological composition which comprises:

(I) up to 10% by weight, based on a total weight of the composition, of one or more $C_{12}$-$C_{40}$ fatty acids, (II) from 0.1% to 10% by weight, based on a total weight of the composition, of one or more $C_{12}$-$C_{40}$ fatty alcohols, (III) from 0.01% to 10% by weight, based on a total weight of the composition, of at least one of an amphiphilic polymer, an associative polymer and a siloxane elastomer, (IV) at least one of sodium hydroxide and potassium hydroxide, (V) from 0.1% to 10% by weight, based on a total weight of the composition, of one or more $C_{12}$-$C_{40}$ polyethoxylated fatty acid esters having a polyethoxy chain length of from 10 to 100, (VI) optionally, at least one low molecular weight surfactant, and (VII) from 0.1% to 30% by weight of at least one of a pigment and a dye.

The present invention also provides a second cosmetic or dermatological composition which comprises:

(I) up to 12% by weight, based on a total weight of the composition, of one or more $C_{12}$-$C_{40}$ fatty acids, (II) from 0% to 3% by weight, based on a total weight of the composition, of one or more $C_{12}$-$C_{40}$ fatty alcohols, (III) from 0.01% to 10% by weight, based on a total weight of the composition, of at least one of an amphiphilic polymer, an associative polymer and a siloxane elastomer, (IV) at least one of sodium hydroxide and potassium hydroxide, and (VII) from 0.1% to 30% by weight of at least one of a pigment and a dye.

In one aspect of the above compositions, component (I) may comprise stearic acid and/or palmitic acid, and/or component (II) may comprise one or more of myristyl alcohol, cetyl alcohol, behenyl alcohol, stearyl alcohol and cetearyl alcohol, and/or component (III) may comprise one or more of dimethicone/vinyl dimethicone crosspolymer, polysilicone-11, acrylate/$C_{10\text{-}30}$ alkyl acrylate crosspolymer, acrylate/vinyl isodecanoate crosspolymer, acrylate/steareth-20 methacrylate copolymer, acrylate/steareth-20 itaconate copolymer, acrylate/steareth-50 acrylate copolymer, acrylate/palmeth-25 acrylate copolymer, steareth-10 alkyl ether/acrylate copolymer, PEG-120 methylglucose dioleate, PEG-60 sorbitan tetraoleate, PEG-150 pentaerythrityl tetrastearate, PEG-55 propylene glycol oleate, PEG-150 distearate and PEG-180/laureth-50 TMMG copolymer, and/or component (IV) may comprise sodium hydroxide and/or component (VII) may comprise one or more of coated mica particles, $TiO_2$ particles, $Fe_2O_3$ particles, zinc oxide-coated $SiO_2$ particles, iron pearlescent pigments prepared without the use of mica and aluminum pearlescent pigments.

In another aspect of the first composition, component (V) may comprise PEG-30 stearate, PEG-40 stearate and/or PEG-100 stearate.

In yet another aspect of the first composition, component (VI) may comprise steareth-2, laureth-4 and/or ceteth-3, preferably at least laureth-4.

In a still further aspect of the first composition, the ratio (I):(II):(V) may be from 5:1:1 to 1:1:5, e.g., from 3:1:1 to 3:1:3, or from 3:1:1 to 1:1:3.

In another aspect of the above compositions, component (VII) may be present in an amount of from 0.5% to 15% by weight, e.g., from 1.0% to 5.0% by weight.

In yet another aspect of the above compositions, component (I) may be present in an amount of from 0.1% to 10% by weight.

In another aspect of the first composition, component (II) may be present in an amount of from 0.1% to 5% by weight, e.g., in an amount of up to 3% by weight, and/or component (V) may be present in an amount of up to 5% by weight.

In a still further aspect of the first and second compositions of the present invention, these compositions may comprise from 0.01% to 5% by weight of an amphiphilic polymer and/or an associative polymer, for example, 0.1% to 1% by weight thereof. Alternatively or cumulatively, these compositions may comprise at least 0.5% by weight of a siloxane elastomer.

In another aspect of the first composition, the composition may comprise:
(I) up to 10% by weight of stearic acid and/or palmitic acid,
(II) from 0.1% to 10% by weight of one or more of cetyl alcohol, behenyl alcohol, stearyl alcohol and cetearyl alcohol,
(III) from 0.01% to 10% by weight of one or more of dimethicone/vinyl dimethicone crosspolymer, polysilicone-11, acrylate/alkyl acrylate crosspolymer, acrylate/vinyl isodecanoate crosspolymer, acrylate/steareth-20 methacrylate copolymer, acrylate/steareth-20 itaconate copolymer, acrylate/steareth-50 acrylate copolymer, acrylate/palmeth-25 acrylate copolymer, steareth-10 alkyl ether/acrylate copolymer, PEG-120 methylglucose dioleate, PEG-60 sorbitan tetraoleate, PEG-150 pentaerythrityl tetrastearate, PEG-55 propylene glycol oleate, PEG-150 distearate and PEG-180/laureth-50/TMMG copolymer,
(IV) from 0.15% to 1% by weight of sodium hydroxide,
(V) up to 10% by weight of one or more of PEG-20 stearate, PEG-40 stearate and PEG-100 stearate,
(VI) from 0% to 10% by weight of one or more of steareth-2, laureth-4 and ceteth-3, and
(VII) from 1.0% to 5.0% by weight of a pigment and/or a dye.

In another aspect of the second composition, the composition may comprise:
(I) up to 12% by weight of stearic acid and/or palmitic acid,
(II) from 0% to 3% by weight of one or more of cetyl alcohol, behenyl alcohol, stearyl alcohol and cetearyl alcohol,
(III) from 0.01% to 10% by weight of one or more of dimethicone/vinyl dimethicone crosspolymer, polysilicone-11, acrylate/alkyl acrylate crosspolymer, acrylate/vinyl isodecanoate crosspolymer, acrylate/steareth-20 methacrylate copolymer, acrylate/steareth-20 itaconate copolymer, acrylate/steareth-50 acrylate copolymer, acrylate/palmeth-25 acrylate copolymer, steareth-10 alkyl ether/acrylate copolymer, PEG-120 methylglucose dioleate, PEG-60 sorbitan tetraoleate, PEG-150 pentaerythrityl tetrastearate, PEG-55 propylene glycol oleate, PEG-150 distearate and PEG-180/laureth-50/TMMG copolymer,
(IV) 0.25% to 1% by weight of sodium hydroxide, and
(VII) from 1.0% to 5.0% by weight of at least one of a pigment and a dye.

In yet another aspect of the present compositions, the compositions may comprise sodium hydroxide as the only neutralizing agent.

In a still further aspect of the present compositions, not more than 9% of the one or more fatty acids may be saponified.

In another aspect, the present compositions may further comprise up to 30% by weight of a non-polar lipid having a polarity of at least 30 mN/m, a mineral oil, a silicone oil and/or a wax. The non-polar lipid and the wax may be selected from non-polar hydrocarbons, hydrogenated polyisobutene, squalane, cyclomethicones, dimethicones, methyl palmitate and dimethiconol stearate. Still further, the lipid phase of the composition may comprise up to 60% by weight, based on the total weight of the lipid phase, of one or more polar lipids having a polarity of at most 30 mN/m.

In yet another aspect, the compositions of the present invention may further comprise a solubilizer, e.g., PEG-40 hydrogenated castor oil, and/or the compositions may further comprise a photoprotective filter, a moisturizer, an active ingredient, a powder raw material, a preservative, a filler and/or a deodorant.

In a still further aspect, the compositions may further comprise ethanol in an amount of up to 30% by weight.

The present invention also provides a decorative cosmetic product, a skin care product, a photoprotective product, and a cleansing emulsion, all of which comprise one of the compositions of the present invention.

It is characteristic that such pearlescent preparations for the purposes of the present invention are advantageously free from mono- and/or di-fatty acid esters of glycerol and/or glycol. These customarily used emulsifiers and/or pearlescence-imparting agents are advantageously not used in order to ensure the pearlescent effect according to the invention in the above formulations. Particular preference is given to preparations according to the invention which comprise no glyceryl stearate, glyceryl distearate, glyceryl isostearate, glyceryl diisostearate, glyceryl oleate, glyceryl palmitate, glyceryl myristate, glyceryl lanolate and/or glyceryl laurate.

The essential advantage of the preparations according to the invention lies in the possibility, shown for the first time, that sodium hydroxide solution may be present as exclusive neutralizing agent without accepting losses with regard to long-term stability, cosmetic pearlescence optics and, in particular, skin compatibility.

Through the addition of pigments and/or dyes (VII) and the innovative combinations resulting therefrom with the other constituents (I, II, III, IV and optionally V), a synergism is produced which makes it possible for the first time to ensure an optically pleasing pearlescence both on the skin and also within the product. This gives the user for the first time the possibility of discerning the optical effects achieved on the skin just from the product.

Usually, the addition of pigments which are present in platelet form to classical emulsions without pearlescence structures does not produce optical effects within the product. The platelets are present in a disordered manner and are not lined up. In the pearlescent emulsions described according to the invention, the pigment platelets are lined up along the lamellar structures corresponding to the matrix of pearlescence. As a result of this, the light is reflected and enhances optical pearlescent effects within the product. The combination of pearlescent emulsions and shimmer pigments thus produces synergistic effects which enhance the optical impression within the product.

The cosmetic and dermatological preparations according to the invention, comprise dyes and/or colour pigments, particularly when they are in the form of decorative cosmetics, but also in the form of face, body care, and photoprotective products. The dyes and colour pigments can be chosen from the corresponding positive list of the Cosmetics Directive or the EC list of cosmetic colorants. In most cases they are identical to the dyes approved for foods. Advantageous colour pigments are, for example, titanium dioxide, mica, iron oxides (e.g. $Fe_2O_3$, $Fe_3O_4$, FeO(OH)) and/or tin oxide. Advantageous dyes are, for example, carmine, Berlin blue, chrome oxide green, ultramarine blue and/or manganese violet. It is particularly advantageous to choose the dyes and/or colour pigments from the following list. The Colour Index Numbers (CIN) are taken from the *Rowe Colour Index,* 3rd Edition, Society of Dyers and Colourists, Bradford, England, 1971.

| Chemical or other name | CIN | Colour |
|---|---|---|
| Pigment Green | 10006 | green |
| Acid Green 1 | 10020 | green |
| 2,4-Dinitrohydroxynaphthalene-7-sulphonic acid | 10316 | yellow |
| Pigment Yellow 1 | 11680 | yellow |
| Pigment Yellow 3 | 11710 | yellow |
| Pigment Orange 1 | 11725 | orange |
| 2,4-Dihydroxyazobenzene | 11920 | orange |
| Solvent Red 3 | 12010 | red |
| 1-(2'-Chloro-4'-nitro-1'-phenylazo)-2-hydroxynaphthalene | 12085 | red |
| Pigment Red 3 | 12120 | red |
| Ceres red; Sudan red; Fat Red G | 12150 | red |
| Pigment Red 112 | 12370 | red |
| Pigment Red 7 | 12420 | red |
| Pigment Brown 1 | 12480 | brown |
| 4-(2'-Methoxy-5'-sulphodiethylamido-1'-phenylazo)-3-hydroxy-5''-chloro-2'',4''-dimethoxy-2-naphthanilide | 12490 | red |
| Disperse Yellow 16 | 12700 | yellow |
| 1-(4-Sulpho-1-phenylazo)-4-aminobenzene-5-sulphonic acid | 13015 | yellow |
| 2,4-Dihydroxyazobenzene-4'-sulphonic acid | 14270 | orange |
| 2-(2,4-Dimethylphenylazo-5-sulpho)-1-hydroxynaphthalene-4-sulphonic acid | 14700 | red |
| 2-(4-Sulpho-1-naphthylazo)-1-naphthol-4-sulphonic acid | 14720 | red |
| 2-(6-Sulpho-2,4-xylylazo)-1-naphthol-5-sulphonic acid | 14815 | red |
| 1-(4'-Sulphophenylazo)-2-hydroxynaphthalene | 15510 | orange |
| 1-(2-Sulpho-4-chloro-5-carboxy-1-phenylazo)-2-hydroxynaphthalene | 15525 | red |
| 1-(3-Methylphenylazo-4-sulpho)-2-hydroxynaphthalene | 15580 | red |
| 1-(4',(8')-Sulphonaphthylazo)-2-hydroxynaphthalene | 15620 | red |
| 2-Hydroxy-1,2'-azonaphthalene-1'-sulphonic acid | 15630 | red |
| 3-Hydroxy-4-phenylazo-2-naphthylcarboxylic acid | 15800 | red |
| 1-(2-Sulpho-4-methyl-1-phenylazo)-2-naphthylcarboxylic acid | 15850 | red |
| 1-(2-Sulpho-4-methyl-5-chloro-1-phenylazo)-2-hydroxynaphthalene-3-carboxylic acid | 15865 | red |
| 1-(2-Sulpho-1-naphthylazo)-2-hydroxynaphthalene-3-carboxylic acid | 15880 | red |
| 1-(3-Sulpho-1-phenylazo)-2-naphthol-6-sulphonic acid | 15980 | orange |
| 1-(4-Sulpho-1-phenylazo)-2-naphthol-6-sulphonic acid | 15985 | yellow |
| Allura Red | 16035 | red |
| 1-(4-Sulpho-1-naphthylazo)-2-naphthol-3,6-disulphonic acid | 16185 | red |
| Acid Orange 10 | 16230 | orange |
| 1-(4-Sulpho-1-naphthylazo)-2-naphthol-6,8-disulphonic acid | 16255 | red |
| 1-(4-Sulpho-1-naphthylazo)-2-naphthol-3,6,8-trisulphonic acid | 16290 | red |
| 8-Amino-2-phenylazo-1-naphthol-3,6-disulphonic acid | 17200 | red |
| Acid Red 1 | 18050 | red |
| Acid Red 155 | 18130 | red |
| Acid Yellow 121 | 18690 | yellow |
| Acid Red 180 | 18736 | red |
| Acid Yellow 11 | 18820 | yellow |
| Acid Yellow 17 | 18965 | yellow |
| 4-(4-Sulpho-1-phenylazo)-1-(4-sulphophenyl)-5-hydroxy-pyrazolone-3-carboxylic acid | 19140 | yellow |
| Pigment Yellow 16 | 20040 | yellow |
| 2,6-(4'-Sulpho-2'', 4''-dimethyl)bisphenylazo)-1,3-dihydroxybenzene | 20170 | orange |
| Acid Black 1 | 20470 | black |

-continued

| Chemical or other name | CIN | Colour |
|---|---|---|
| Pigment Yellow 13 | 21100 | yellow |
| Pigment Yellow 83 | 21108 | yellow |
| Solvent Yellow | 21230 | yellow |
| Acid Red 163 | 24790 | red |
| Acid Red 73 | 27290 | red |
| 2-[4'-(4''-Sulpho-1''-phenylazo)-7'-sulpho-1'-naphthylazo]-1-hydroxy-7-aminonaphthalene-3,6-disulphonic acid | 27755 | black |
| 4'-[(4''-Sulpho-1''-phenylazo)-7'-sulpho-1'-naphthylazo]-1-hydroxy-8-acetylaminonaphthalene-3,5-disulphonic acid | 28440 | black |
| Direct Orange 34, 39, 44, 46, 60 | 40215 | orange |
| Food Yellow | 40800 | orange |
| trans-β-Apo-8'-carotenaldehyde ($C_{30}$) | 40820 | orange |
| trans-Apo-8'-carotenic acid ($C_{30}$)-ethyl ester | 40825 | orange |
| Canthaxanthin | 40850 | orange |
| Acid Blue 1 | 42045 | blue |
| 2,4-Disulpho-5-hydroxy-4'-4''-bis(diethylamino)triphenylcarbinol | 42051 | blue |
| 4-[(4-N-Ethyl-p-sulphobenzylamino)phenyl(4-hydroxy-2-sulphophenyl)(methylene)-1-(N-ethyl-N-p-sulphobenzyl)-2,5-cyclohexadienimine] | 42053 | green |
| Acid Blue 7 | 42080 | blue |
| (N-Ethyl-p-sulphobenzylamino)phenyl(2-sulphophenyl)methylene-(N-ethyl-N-p-sulphobenzyl)$\Delta^{2,5}$-cyclohexadienimine | 42090 | blue |
| Acid Green 9 | 42100 | green |
| Diethyldisulphobenzyldi-4-amino-2-chlorodi-2-methyl-fuchsonimmonium | 42170 | green |
| Basic Violet 14 | 42510 | violet |
| Basic Violet 2 | 42520 | violet |
| 2'-Methyl-4'-(N-ethyl-N-m-sulphobenzyl)amino-4''-(N-diethyl)amino-2-methyl-N-ethyl-N-m-sulphobenzylfuchsonimmonium | 42735 | blue |
| 4'-(N-Dimethyl)amino-4''-(N-phenyl)aminonaphtho-N-dimethyl-fuchsonimmonium | 44045 | blue |
| 2-Hydroxy-3,6-disulpho-4,4'-bisdimethylaminonaphtho-fuchsonimmonium | 44090 | green |
| Acid Red 52 | 45100 | red |
| 3-(2'-Methylphenylamino)-6-(2'-methyl-4'-sulphophenylamino)-9-(2''-carboxyphenyl)xanthenium salt | 45190 | violet |
| Acid Red 50 | 45220 | red |
| Phenyl-2-oxyfluorone-2-carboxylic acid | 45350 | yellow |
| 4,5-Dibromofluorescein | 45370 | orange |
| 2,4,5,7-Tetrabromofluorescein | 45380 | red |
| Solvent Dye | 45396 | orange |
| Acid Red 98 | 45405 | red |
| 3',4',5',6',-Tetrachloro-2,4,5,7-tetrabromofluorescein | 45410 | red |
| 4,5-Diiodofluorescein | 45425 | red |
| 2,4,5,7-Tetraiodofluorescein | 45430 | red |
| Quinophthalone | 47000 | yellow |
| Quinophthalonedisulphonic acid | 47005 | yellow |
| Acid Violet 50 | 50325 | violet |
| Acid Black 2 | 50420 | black |
| Pigment Violet 23 | 51319 | violet |
| 1,2-Dioxyanthraquinone, calcium-aluminium complex | 58000 | red |
| 3-Oxypyrene-5,8,10-sulphonic acid | 59040 | green |
| 1-Hydroxy-4-N-phenylaminoanthraquinone | 60724 | violet |
| 1-Hydroxy-4-(4'-methylphenylamino)anthraquinone | 60725 | violet |
| Acid Violet 23 | 60730 | violet |
| 1,4-Di(4'-methylphenylamino)anthraquinone | 61565 | green |
| 1,4-Bis(o-sulpho-p-toluidino)anthraquinone | 61570 | green |
| Acid Blue 80 | 61585 | blue |
| Acid Blue 62 | 62045 | blue |
| N,N'-Dihydro-1,2,1',2'-anthraquinone azine | 69800 | blue |
| Vat Blue 6; Pigment Blue 64 | 69825 | blue |
| Vat Orange 7 | 71105 | orange |
| Indigo | 73000 | blue |
| Indigo disulphonic acid | 73015 | blue |
| 4,4'-Dimethyl-6,6'-dichlorothioindigo | 73360 | red |
| 5,5'-Dichloro-7,7'-dimethylthioindigo | 73385 | violet |
| Quinacridone Violet 19 | 73900 | violet |
| Pigment Red 122 | 73915 | red |
| Pigment Blue 16 | 74100 | blue |
| Phthalocyanine | 74160 | blue |
| Direct Blue 86 | 74180 | blue |
| Chlorinated phthalocyanine | 74260 | green |
| Natural Yellow 6,19; Natural Red 1 | 75100 | yellow |
| Bixin, Norbixin | 75120 | orange |
| Lycopene | 75125 | yellow |
| Trans-alpha-, beta- and gamma-carotene | 75130 | orange |
| Keto- and/or hydroxyl derivatives of carotene | 75135 | yellow |

-continued

| Chemical or other name | CIN | Colour |
|---|---|---|
| Guanine or pearlescent agent | 75170 | white |
| 1,7-Bis(4-hydroxy-3-methoxyphenyl)-1,6-heptadiene-3,5-dione | 75300 | yellow |
| Complex salt (Na, Al, Ca) of carminic acid | 75470 | red |
| Chlorophyll a and b; copper compounds of chlorophylls and chlorophyllins | 75810 | green |
| Aluminium | 77000 | white |
| Hydrated alumina | 77002 | white |
| Hydrous aluminium silicates | 77004 | white |
| Ultramarine | 77007 | blue |
| Pigment Red 101 and 102 | 77015 | red |
| Barium sulphate | 77120 | white |
| Bismuth oxychloride and its mixtures with mica | 77163 | white |
| Calcium carbonate | 77220 | white |
| Calcium sulphate | 77231 | white |
| Carbon | 77266 | black |
| Pigment Black 9 | 77267 | black |
| Carbo medicinalis vegetabilis | 77268:1 | black |
| Chromium oxide | 77288 | green |
| Chromium oxide, hydrous | 77289 | green |
| Pigment Blue 28, Pigment Green 14 | 77346 | green |
| Pigment Metal 2 | 77400 | brown |
| Gold | 77480 | brown |
| Iron oxides and hydroxides | 77489 | orange |
| Iron oxide | 77491 | red |
| Hydrated iron oxide | 77492 | yellow |
| Iron oxide | 77499 | black |
| Mixtures of iron (II) and iron(III) hexacyanoferrate | 77510 | blue |
| Pigment White 18 | 77713 | white |
| Manganese anmonium diphosphate | 77742 | violet |
| Manganese phosphate; $Mn_3(PO_4)_2 \cdot 7 H2O$ | 77745 | red |
| Silver | 77820 | white |
| Titanium dioxide and its mixtures with mica | 77891 | white |
| Zinc oxide | 77947 | white |
| 6,7-Dimethyl-9-(1'-D-ribityl)isoalloxazine, lactoflavin | | yellow |
| Sugar colouring | | brown |
| Capsanthin, capsorubin | | orange |
| Betanin | | red |
| Benzopyrylium salts, anthocyans | | red |
| Aluminium, zinc, magnesium and calcium stearate | | white |
| Bromothymol blue | | blue |
| Bromocresol green | | green |
| Acid Red 195 | | red |

If the formulations according to the invention are in the form of products, which are intended for use in the facial area, it is favourable to choose one or more substances from the following group as the dye: 2,4-dihydroxyazobenzene, 1-(2'-chloro-4'-nitro-1'-phenyl-azo)-2-hydroxynaphthalene, Ceres Red, 2-(4-sulpho-1-naphthylazo)-1-naphthol-4-sulphonic acid, calcium salt of 2-hydroxy-1,2'-azonaphthalene-1'-sulphonic acid, calcium and barium salts of 1-(2-sulpho-4-methyl-1-phenylazo)-2-naphthylcarboxylic acid, calcium salt of 1-(2-sulpho-1-naphthylazo)-2-hydroxynaphthalene-3-carboxylic acid, aluminium salt of 1-(4-sulpho-1-phenylazo)-2-naphthol-6-sulphonic acid, aluminium salt of 1-(4-sulpho-1-naphthylazo)-2-naphthol-3,6-disulphonic acid, 1-(4-sulpho-1-naphthylazo)-2-naphthol-6,8-disulphonic acid, aluminium salt of 4-(4-sulpho-1-phenylazo)-1-(4-sulphophenyl)-5-hydroxypyrazolone-3-carboxylic acid, aluminium and zirconium salts of 4,5-dibromofluorescein, aluminium and zirconium salts of 2,4,5,7-tetrabromofluorescein, 3',4',5',6'-tetrachloro-2,4,5,7-tetrabromofluorescein and its aluminium salt, aluminium salt of 2,4,5,7-tetraiodofluorescein, aluminium salt of quinophthalone disulphonic acid, aluminium salt of indigo disulphonic acid, red and black iron oxide (CIN: 77 491 (red) and 77 499 (black)), hydrated iron oxide (CIN: 77 492), manganese ammonium diphosphate and titanium dioxide.

Also advantageous are oil-soluble natural dyes, such as, for example, paprika extracts, β-carotene or cochenille.

Also advantageous for the purposes of the present invention are formulations with a content of pearlescent pigments. Preference is given in particular to the types of pearlescent pigments listed below:

1. Natural pearlescent pigments, such as, for example
   "pearl essence" (guanine/hypoxanthine mixed crystals from fish scales) and
   "mother of pearl" (ground mussel shells)
2. Monocrystalline pearlescent pigments, such as, for example, bismuth oxychloride (BiOCl)
3. Layer-substrate pigments: e.g. mica/metal oxide Bases for pearlescent pigments are, for example, pulverulent pigments or castor oil dispersions of bismuth oxychloride and/or titanium dioxide, and bismuth oxychloride and/or titanium dioxide on mica. The lustre pigment listed under CIN 77163, for example, is particularly advantageous.

Also advantageous are, for example, the following types of pearlescent pigment based on mica/metal oxide:

| Group | Coating/layer thickness | Colour |
| --- | --- | --- |
| Silver-white pearlescent pigments | $TiO_2$: 40-60 nm | silver |
| Interference pigments | $TiO_2$: 60-80 nm | yellow |
| | $TiO_2$: 80-100 nm | red |
| | $TiO_2$: 100-140 nm | blue |
| | $TiO_2$: 120-160 nm | green |
| Colour lustre pigments | $Fe_2O_3$ | bronze |
| | $Fe_2O_3$ | copper |
| | $Fe_2O_3$ | red |
| | $Fe_2O_3$ | red-violet |
| | $Fe_2O_3$ | red-green |
| | $Fe_2O_3$ | black |
| Combination pigments | $TiO_2/Fe_2O_3$ | gold shades |
| | $TiO_2/Cr_2O_3$ | green |
| | $TiO_2$/Berlin blue | deep blue |
| | $TiO_2$/carmine | red |

Particular preference is given, for example, to the pearlescent pigments available from Merck under the trade names Timiron, Colorona or Dichrona.

The list of given pearlescent pigments is not of course intended to be limiting. Pearlescent pigments which are advantageous for the purposes of the present invention are obtainable by numerous methods known per se. For example, other substrates apart from mica can also be coated with further metal oxides, such as, for example, silica and the like. $SiO_2$ particles coated with, for example, $TiO_2$ and $Fe_2O_3$ ("Ronaspheren"), which are marketed by Merck and are particularly suitable for the optical reduction of fine lines are advantageous.

It can moreover be advantageous to dispense completely with a substrate such as mica. Preference is given to iron pearlescent pigments prepared without the use of mica. Such pigments are available, for example, under the trade name Sicopearl Kupfer 1000 from BASF. Particular preference is given to alumina pearlescent pigments prepared without the use of mica. Such pigments are available, for example, under the trade name Xirona from Merck.

In addition, also particularly advantageous are effect pigments which are obtainable under the trade name Metasomes Standard/Glitter in various colours (yellow, red, green, blue) from Flora Tech. The glitter particles are present here in mixtures with various auxiliaries and dyes (such as, for example, the dyes with the Colour Index (CI) Numbers 19140, 77007, 77289, 77491).

The dyes and pigments may be present either individually or in a mixture, and can be mutually coated with one another, different coating thicknesses generally giving rise to different colour effects. The total amount of dyes and colour-imparting pigments is advantageously chosen from the range from e.g. 0.1% by weight to 30% by weight, preferably from 0.5 to 15% by weight, in particular from 1.0 to 5% by weight, in each case based on the total weight of the preparations.

Very particularly preferred pigments are pearlescent pigments
  based on coated mica which are available from Merck under the trade names Timiron, Colorona or Dichrona (e.g. mica coated with titanium dioxide, tin oxide, silica, etc.)
  $TiO_2$ and $Fe_2O_3$ and/or tin oxide-coated $SiO_2$ particles ("Ronaspheren"),
  iron pearlescent pigments prepared without the use of mica. Such pigments are available, for example, under the trade name Sicopearl Kupfer 1000 from BASF.

Particular preference is given to aluminium pearlescent pigments prepared without the use of mica, such as, for example, alumina, aluminium oxide e.g. coated with titanium dioxide and tin oxide. Such pigments are available, for example, under the trade name Xirona from Merck.

Suitable $C_{12}$-$C_{40}$ fatty acids (I) are completely neutralized, partially neutralized or unneutralized, branched and/or unbranched, saturated and/or unsaturated fatty acids with a chain length of from 12 to 40 carbon atoms.

The fatty acid(s) are preferably chosen from the group of acids which are completely or partially neutralized with customary alkalis (such as, for example, sodium hydroxide and/or potassium hydroxide, sodium carbonate and/or potassium carbonate). For example, stearic acid and stearates, isostearic acid and isostearates, palmitic acid and palmitates, and myristic acid and myristates are particularly advantageous. Through the preparations according to the invention, it is possible for the first time to dispense with the use of mono- and/or triethanolamine as neutralizing agent. This achieves improved skin compatibility but good long-term stability and excellent pearlescence nevertheless.

Preference is given to using C16/C18 fatty acids and mixtures, in particular in a eutectic mixture, very particularly preferably stearic acid and palmitic acid.

In the fatty acids used, the saponified fraction is preferably a maximum of 9%.

The $C_{12}$-$C_{40}$ fatty acids (I) are used in an amount of up to 12% by weight, preferably from 0.1-10% by weight, based on the total preparation.

The $C_{12}$-$C_{40}$ fatty alcohols (II) chosen are alcohols from the group of saturated and/or unsaturated, branched and/or unbranched fatty alcohols with a chain length of from 12 to 40 carbon atoms. Preferably, C14-C20 fatty alcohols are chosen.

The fatty alcohols are preferably chosen according to the invention from the following group: myristyl alcohol behenyl alcohol ($C_{22}H_{45}OH$), cetearyl alcohol [a mixture of cetyl alcohol ($C_{16}H_{33}OH$) and stearyl alcohol ($C_{18}H_{37}OH$)], lanolin alcohols (wool wax alcohols, which represent the unsaponifiable alcohol fraction of wool wax which is obtained following saponification of wool wax). Particular preference is given to cetyl alcohol and cetylstearyl alcohol.

The $C_{12}$-$C_{40}$ fatty alcohols (II) are used in an amount of up to 10% by weight, preferably from 0.1-5% by weight, or up to 3% by weight, based on the total preparation.

The $C_{12}$-$C_{40}$ POE fatty acid esters (V) chosen are polyethoxylated fatty acid esters with a chain length of from 12 to 40 carbon atoms and with a degree of ethoxylation of from 10 to 100. From the group of polyethoxylated fatty acid esters, the following are preferably chosen: PEG-9 stearate, PEG-8 distearate, PEG-20 stearate, PEG-8 stearate, PEG-8 oleate, PEG-25 glyceryl trioleate, PEG-40 sorbitan lanolate, PEG-15 glyceryl ricinoleate, PEG-20 glyceryl stearate, PEG-20 glyceryl isostearate, PEG-20 glyceryl oleate, PEG-20 stearate, PEG-20 methylglucose sesquistearate, PEG-30 glyceryl isostearate, PEG-20 glyceryl laurate, PEG-30 stearate, PEG-30 glyceryl stearate, PEG-40 stearate, PEG-30 glyceryl laurate, PEG-50 stearate, PEG-100 stearate, PEG-150 laurate. Polyethoxylated stearic esters, for example, are particularly advantageous.

Particular preference is given to PEG-40 stearates.

The $C_{12}$-$C_{40}$ POE fatty acid esters (V) are used in an amount of up to 10% by weight, preferably from 0.1-5% by weight, based on the total preparation.

In one tried and tested preparation, the constituents I, II and V are in the ratio (I:II:V) 5:1:1 to 1:1:5. Ratios of I:II:V in the range 3:1:1 to 3:1:3 or in the range 3:1:1 to 1:1:3 are particularly preferred.

This targeted mixing generates synergistic effects with regard to the positive properties of the cosmetic preparation.

The amphiphilic polymers and/or associative polymers (III) chosen are polymers which carry at least one fatty acid or fatty alcohol group, as hydrophobic group, and one hydrophilic group. The polymers are water-soluble or can be dispersed in water as microgels. These polymers are referred to as swellable. The polymers can be composed of any chemical nature, e.g. free-radical polymers, vinyl or acrylic polymers, polycondensates and/or mixtures thereof. The polymers may have an ionic or nonionic structure, preference being given to anionic and nonionic polymers.

Preferably, the amphiphilic and/or associative polymers may be chosen from:

Cellulose ethers comprising hydrophobic substituents, such as alkyl groups with a carbon number greater than or equal to 8, such as, for example, hydroxyethylcellulose Natrosol Plus Grade 330 from Aqualon.

Quaternized cationic cellulose with at least one fatty acid group, such as alkyl, arylalkyl or alkylaryl groups or mixtures thereof, preferably with a carbon number of C8-C22.

Quaternized alkylhydroxyethylcelluloses, as available, for example, under the name Quatrisoft LM 200, Quatrisoft LM-X 529-18-A, Quatrisoft LM-X 529-18-B (C12 alkyl) and/or Quatrisoft LM-X 529-8 (C18 alkyl) from Amerchol. Preference is likewise given to quaternized alkylhydroxyethylcellulose which are available under the names Crodacel QM, Crodacel QL (C12 alkyl) and/or Crodacel QS (C18 alkyl) from Croda.

Galactomannans comprising hydrophobic substituents, in particular the derivatives as are disclosed in EP-A-281360.

Pullulans modified by hydrophobic groups, in particular cholesterol groups.

Gelatins modified by hydrophobic groups, in particular C6-C18 alkyl groups;

mucopolysaccharides obtained from glycosaminoglycans and hyaluronic acid.

In addition, those associative and/or amphiphilic polymers as are disclosed in EP-BL-1046387, which are hereby explicitly included in the disclosure content of the present invention, can be preferably used.

Particularly suitable associative polymers have proven to be those chosen from the group:

of polyethylene glycol ethers of the general formula R—O—(—CH$_2$—CH$_2$—O—)$_n$—R', where R and R', independently of one another, are branched or unbranched alkyl, aryl or alkenyl radicals and n is a number greater than 100, of etherified fatty acid ethoxylates of the general formula R—COO—(—CH$_2$—CH$_2$—O—)$_n$—R', where R and R', independently of one another, are branched or unbranched alkyl, aryl or alkenyl radicals and n is a number greater than 100, of esterified fatty acid ethoxylates of the general formula R—COO—(—CH$_2$—CH$_2$—O—)$_n$—C(O)—R', where R and R', independently of one another are branched or unbranched alkyl, aryl or alkenyl radicals and n is a number greater than 100, of polypropylene glycol ethers of the general formula R—O—(—CH$_2$—CH(CH$_3$)—O—)$_n$—R', where R and R', independently of one another, are branched or unbranched alkyl, aryl or alkenyl radicals and n is a number greater than 100, of esterified fatty acid propoxylates of the general formula R—COO—(—CH$_2$—CH(CH$_3$)—O—)$_n$—C(O)—R', where R and R', independently of one another, are branched or unbranched alkyl, aryl or alkenyl radicals and n is a number greater than 100, of polypropylene glycol ethers of the general formula R—O—X$_n$—Y$_m$—R', where R and R', independently of one another, are branched or unbranched alkyl, aryl or alkenyl radicals, where X and Y are not identical and are in each case either an oxyethylene group or an oxypropylene group and n and m, independently of one another, are numbers, the sum of which is greater than 100 of etherified fatty acid propoxylates of the general formula R—COO—X$_n$—Y$_m$—R', where R and R', independently of one another, are branched or unbranched alkyl, aryl or alkenyl radicals, where X and Y are not identical and are in each case either an oxyethylene group or an oxypropylene group and n and m, independently of one another, are numbers, the sum of which is greater than 100 tetramethoxymethylglycoluril

Advantageous polymers according to the invention are characterized in particular by the following structural formula

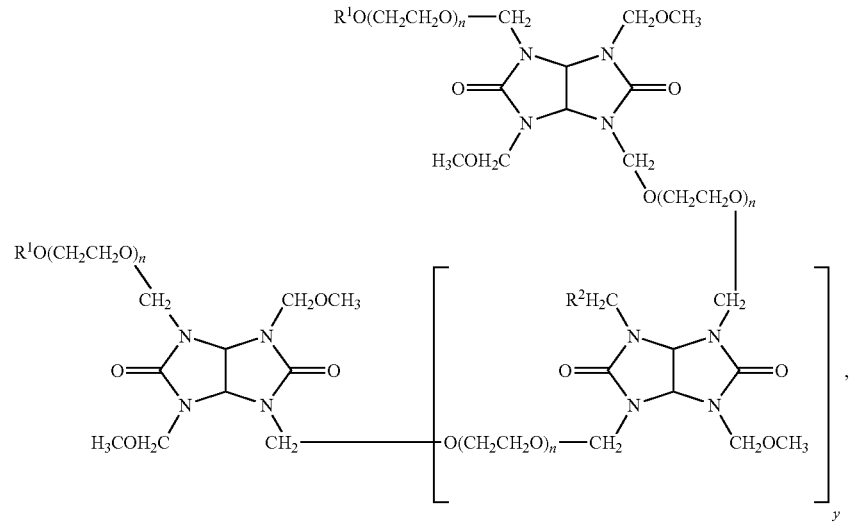

in which $R^1$ is a branched or unbranched, saturated or unsaturated alkyl radical having 4 to 40 carbon atoms, $R^2$=—$OCH_3$ or —$O(CH_2CH_2O)_xR^1$, x is an integer from 1 to 100, n is an integer from 100 to 250 and y is on average 2 or 3.

Particularly advantageous polymers according to the invention are those for which n is an integer from 150 to 200. It is particularly advantageous for the purposes of the present invention if, moreover, $R^1$ is a branched or unbranched, saturated or unsaturated alkyl radical having 8 to 12 carbon atoms.

It is also advantageous for the purposes of the present invention if the average molar mass of the polymers is between 30 000 and 50 000.

According to the invention, PEG-180/octoxynol-40/tetramethoxymethylglycoluril copolymers where $R^2$=—$O(CH_2CH_2O)_{40}C_8H_{17}$ and n=180 are very particularly advantageous.

Also particularly advantageous according to the invention are PEG-180/laureth-50/tetramethoxymethylglycoluril copolymers where $R^2$=—$O(CH_2CH_2O)_{50}C_{12}H_{25}$ and n=180.

According to the invention, polyether-1 is also particularly advantageous.

PEG-150 distearate and PEG-150 dioleate are particularly advantageous. PEG-300 pentaerythrityl tetraisostearate, PEG-120 methylglucose dioleate, PEG-160 sorbitan triisostearate, PEG-450 sorbitol hexaisostearate and PEG-230 glyceryl triisostearate are also to be used advantageously as associative polymers.

It is accordingly also advantageous to choose hydrophobically substituted polysaccharide derivatives as associative thickeners, for example hydrophobically substituted cellulose ethers, hydrophobically substituted starches, alginates, glucans, chitins, dextrans, caseinates, pectins, proteins and gums, and also polyurethanes, polyacrylamides, polyvinyl alcohols, polyacrylates and the like.

The hydrophobically substituted polysaccharide derivatives described in U.S. Pat. No. 5,426,182, which are hereby explicitly included in the disclosure content of the present invention, are particularly advantageous.

It may also in some instances be advantageous if the associative polymer or polymers used according to the invention has or have physiological effectiveness within the meaning of a cosmetic or pharmaceutical effect. Thus, for example, the biosurfactant esters disclosed in DE-A1-4344661 can advantageously be used for the purposes of the present invention.

Preference is given to nonionic polymers such as Pure Thix TX grades, crosspolymers, such as acrylates/vinyl isodecanoate crosspolymer (Stabylen 30 from 3-V-Sigma) and acrylates/C10-C30 alkyl acrylate crosspolymer (Pemulen TR 1, Pemulen TR 2, Ultrez 21, Carbopol ETD 2020, Carbopol ETD 2001 from Noveon), and hydrophobically modified polyacrylates (HASE grades), such as acrylates/steareth-20 methacrylate copolymer (Acrysol and/or Aculyn 22 from Rohm & Haas), acrylates/steareth-20 itaconate copolymer (Structure 2000 from National Starch).

It is advantageous for the purposes of the present invention to choose the total amount of the associative and/or amphiphilic polymers from the range from 0.01 to 5% by weight, advantageously from 0.1 to 1% by weight, in each case based on the total weight of the formulation.

The preferred amphiphilic polymers are listed in Table 1 below, which also lists their trade name besides the structural formula and the INCI name.

TABLE 1

| INCI | Structural formula | Trade name |
|---|---|---|
| Acrylates/Steareth-20 Methacrylate Copolymer | $CO_2R$, $CO_2$—$(CH_2CH_2O)_n$—$CH_2(CH_2)_{16}CH_3$ (with R', $CH_3$ substituents) | Acrysol 22 Polymer (Rohm + Haas) |
| Acrylates/Steareth-20 Itanconate Copolymer | $CO_2R$, $CO_2H$, $CO_2$—$(CH_2CH_2O)_n$—R | Structure 2000 (National Starch) |
| Steareth-10 Ally Ether/Acrylate Copolymer | RO—, $CO_2R'$ | Salcare SC 80 (30% strength) |
| Acrylates/Steareth-50 Acrylate Copolymer | $CO_2H$, $CO_2H$, $CO_2$—$(CH_2CH_2O)_n$—R | Antil 208 (Goldschmidt) (Mixture with Laureth-3, Propylene Glycol) |
| Acrylates/Palmeth-25 Acrylate Copolymer | | Synthalen W 2000 |

TABLE 1-continued

| INCI | Structural formula | Trade name |
|---|---|---|
| Acrylates/ C10–30 Alkyl Acrylates Crosspolymer | structure with $CO_2H$ and $CO_2R$ groups, $CH_3$ | Pemulen Tr-1, Pemulen TR-2, (Noveon) |
| Acrylates/Vinyl Isodecanoate Crosspolymer | | Stabylen 30 |
| Cetylhydroxy-ethyl-cellulose | 48. disaccharide structure with hydroxyethyl and RO-ethyl substituents<br>49. R = —$CH_2CH_2(OH)(CH_2)_{13}CH_3$<br>50. R = —$C_6H_4(CH_2)_3CH_3$ | Natrosol Plus 330 CS (Hercules) |
| other alkyl-modified cellulose derivatives | | |
| "Polyquaternium-24" | | Quatrisoft Polymer LM-200 (Amerchol) |
| PEG-120 Methylglucose Dioleate | methylglucose with $O(CH_2CH_2O)_n$—$C(O)C_{17}H_{33}$ groups, $H(OH_2CH_2C)_n$—O, $H(CH_2CH_2C)_n$—O, $OCH_3$, $O(CH_2CH_2O)_n$—$C(O)C_{17}H_{33}$ | Glucamate DOE-120 (Nordmann & Rassmann) |
| PEG-60 Sorbitan Tetraoleate | sorbitan with four $O(CH_2CH_2O)_n$—$C(O)C_{17}H_{33}$ / $H_{33}C_{17}(O)C$—$(OH_2CH_2C)_n$—O branches | Nikkol GO-460 (Nikko chemicals) |
| PEG-150 Pentaerythrityl Tetrastearate | $H_{35}C_{17}(O)C$—$(OH_2CH_2C)_n$—O— and —O—$(CH_2CH_2O)_n$—$C(O)C_{17}H_{35}$ groups on pentaerythritol core | Crothix, Code ES 2054 (Croda) |

TABLE 1-continued

| INCI | Structural formula | Trade name |
|---|---|---|
| PEG-55 Propylene Glycol Oleate | $C_{17}H_{33}(O)C-[O \frown \frown]_n-O-[\frown O \frown]_n-C(O)C_{17}H_{33}$ with $CH_3$ branch | Antil 141 Liquid Goldschmidt (40% Polymer, 40% Propylene Glycol, 20% water) |
| PEG-180/ Laureth-50/ TMMG Copolymer | (complex bicyclic structure with $R^1CH_2CH_2CH_2$, $CH_2OCH_3$, $R^2H_2C$, $H_2C$, $OCH_2CH_2C$, $CH_3$, $CH_2OCH_3$, $H_2COH_2C$, $CHCH_2CH_2CH_2CH_2$, $CH_2OCH_2$, $H_2COH_2C$, $CHC_2H_2CH_2R^2$ groups)<br>$R^1 = C_nH_{35}$<br>$R^2 = OCH_2$ or $C(CH_2CH_2O)_nR^1$<br>$n = 180$<br>$x = 50$<br>$y = 2-3$ on average | Pure Thix TX 1450 (Süd-Chemie) |
| PEG-150 Distearate | $H_{35}-C_{17}C(O)-O-(H_2CH_2CO)_n-C(O)C_{17}H_{35}$ with $CH_3$ branch | Rewopal PEG 6000 DS |

The use of solid elastomeric polyorganosiloxanes or organopolysiloxanes, referred to below as siloxane elastomers, in cosmetic preparations is known per se and has achieved importance in recent years. Besides being used in cosmetics, these substances have been used in foods and animal feeds, pharmaceuticals, impregnating agents, lubricants and so on. Siloxane elastomers are partially or completely crosslinked and in most cases have a three-dimensional structure. They are obtainable by a reaction of vinyl-terminated polymethylsiloxane and methylhydrodimenthylsiloxane or else by reaction of hydroxy-terminated dimethylpolysiloxane and trimethylsiloxy-terminated methylpolysiloxane:

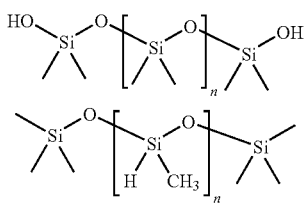

These siloxane elastomers are used, for example, for adjusting the rheological properties of a preparation. Siloxane elastomers of this type are described, for example, in the European patent specification 295886, and the U.S. Pat. No. 5,266,321, which disclose the use of these substances in face-cleansing compositions and oil-containing makeup products. These specifications also describe the nature of siloxane elastomers in more detail. The siloxane elastomers are used in cosmetic preparations in particular due to their pleasant sensory properties, the resulting products are described as velvety, powdery and/or matting. In addition, they have stabilizing effects on formulations with a high content of oil and low water contents of at most 5% by weight. When formulating the abovementioned products, the problem of the siloxane elastomers being incompatible with other frequently used components often arises, which leads to unsatisfactory long-term stability of the products.

These disadvantages known from the prior art have been overcome according to the invention.

In this connection it is preferred when siloxane elastomers chosen from the groups of siloxane elastomers are used (a) which contain units $R_2SiO$ and $RSiO_{1.5}$ and/or $R3SiO_{0.5}$ and/or $SiO_2$, where the individual radicals R are, in each case, independently of one another, hydrogen, alkyl, such as, for example, methyl, ethyl, propyl or aryl, such as, for example, phenyl or tolyl, alkenyl, such as, for example, vinyl, and the weight ratio of the units $R_2SiO$ to $RSiO_{1.5}$ is chosen in the range from 1:1 to 30:1; (b) which are insoluble and swellable in silicone oil and which are obtainable by the addition reaction of an organopolysiloxane (1) which contains silicon-bonded hydrogen with an organopolysiloxane (2) which contains unsaturated aliphatic groups, where the quantitative fractions used are chosen such that the amount of the hydrogen in the organopolysiloxane (1) or in the unsaturated aliphatic groups of the organopolysiloxane (2) is in the range from 1 to 20 mol % if the organopolysiloxane is not cyclic, and is in the range from 1 to 50 mol % if the organopolysiloxane is cyclic. It is particularly preferred when the organopolysiloxane elastomer is used in combination with oils of hydrocarbons of animal and/or vegetable origin, synthetic oils, synthetic esters, synthetic ethers or mixtures thereof. It is very particularly preferred when the organopolysiloxane elastomer is used in combination with unbranched silicone oils which are liquid or pasty at room temperature, or cyclic silicone oils or mixtures thereof. It is very exceptionally preferred when the organopolysiloxane elastomer is used in the form of organopolysiloxane elastomer gel and a lipid phase, where the content of the organopolysiloxane elastomer in the gel is 3 to 80% by weight, very exceptionally preferably 0.3 to 60% by weight.

It is advantageous to use siloxane elastomers from Dow Corning, as are described in the U.S. Pat. No. 5,654,362 and are available under the trade name 9040 Silicone Elastomer Blend, in the formulations according to the invention. Likewise advantageous are siloxane elastomers from Grant Chemical with the INCI name Polysilicone-11, such as the grades Gransil GCM or Gransil PM, as are described in the U.S. Pat. Nos. 5,266,321, 4,980,167 and 4,742,142. Particularly advantageous siloxane elastomers are also those which are present in the form of spherical powders with an average particle size of from 2 to 5 μm and a particle size distribution of from 1 to 15 μm and are described in the Japanese patent specifications 4-66446 and 4-17162, and in the Japanese laid-open specification 2-243612 or are described with an average particle size of less than 50 μm in the specifications EP 0295 886 and U.S. Pat. No. 4,761,454. Commercially available products are, for example, Torayfil E-505C, Torayfil E-506 C from Toray-Dow Corning Silicone Co.

A particularly advantageous siloxane elastomer in the form of spherical powder is dimethicone/vinyldimethicone crosspolymer with a particle size distribution of from 1 to 15 μm, available under the trade name Dow Corning 9509 Powder from Dow Corning. Also advantageous are gels comprising the siloxane elastomers which are available under the trade names KSG-15, -16, -17, -18, -20 from Shin-Etsu or Gransil 5CYCgel, Gransil SR DMF 10gel, Gransil SR DC 556gel from Grant Chemical, SF 839, SF1204, JK113 from General Electric, and lauryl dimethicone/vinyidimethicone crosspolymers, as are available under the names KSG41, 42, -43, -44 from Shin-Etsu. A further advantageous siloxane elastomer is the cyclomethicone+vinyidimethicone/methicone crosspolymer or the chemically related elastomer Crosslinked Stearyl Methyl Dimethyl Siloxane Elastomer as are supplied, for example, by Grant Chemical under the name SR-CYC.

The siloxane elastomers used are also emulsions and/or suspensions which comprise siloxane elastomers. By way of example, preference is given to the emulsions and/or suspensions in Table 2 below.

TABLE 2

| Trade name/ BDF | INCI | Elastomer content |
|---|---|---|
| Dow Corning 9040 Emulsion/ Dow Corning 9040 Concentrated Emulsion | Cyclopentasiloxane (and) Dimethicone Crosspolymer (and) Cyclohexasiloxane (and) Cyclomethicone (and) Dimethicone (and) Laureth-4 (and) Laureth-23 (and) Parabens *) | 70.6% DC 9040; 10.8% DC345; 5.4% DC 200; 1.9% Brij35; 0.8% Brij30; 0.55% Liquapar Optima; 9.95% Water |
| Dow Corning 9509 Silicone Elastomer Suspension/ Dow Corning 9509 | Dimethicone/Vinyl Dimethicone Crosspolymer + C12-14 Pareth-12 | 63% spherical siloxane elastomers in water |

The siloxane elastomers (III) are used in an amount of up to 10% by weight, preferably of 0.5-10% by weight of the pure elastomer, based on the total preparation.

In addition, low molecular weight surfactants (VI), in particular ceteareth-3, ceteareth-6, steareth-2, steareth-10, ceteth-10, isosteareth-10, laureth-2, laureth-3, laureth-4, myreth-4, laneth-5, ceteth-2, ceteth-3, oleth-2, oleth-3 and/or oleth-5 are preferably added to the preparations according to the invention. Laureth-4 is very particularly preferred.

Particularly advantageous preparations are the following formulations, which comprise (I) up to 10% by weight of stearic acid/palmitic acid,
(II) 0.1-10% by weight of cetyl alcohol, behenyl alcohol, stearyl alcohol and/or cetearyl alcohol
(III) 0.01-10% by weight of dimethicone/vinyl dimethicone crosspolymer, polysilicone-11, acrylate/alkyl acrylate crosspolymer, acrylate/vinyl isodecanoate crosspolymer, acrylate/steareth-20 methacrylate copolymer, acrylate/steareth-20 itaconate copolymer, acrylate/steareth-50 acrylate copolymer, acrylate/palmeth-25 acrylate copolymer, steareth-10 ally ether/acrylate copolymer, PEG-120 methylglucose dioleate, PEG-60 sorbitan tetraoleate, PEG-150 pentaerythrityl tetrastearate, PEG-55 propylene glycol oleate, PEG-150 distearate and/or PEG-180/laureth-50/ TMMG copolymer
(IV) 0.15-1% by weight of sodium hydroxide solution
(V) up to 10% by weight of PEG-20 stearate, PEG-40 stearate and/or PEG-100 stearate,
(VII) 1.0 to 5.0% by weight of pigments and/or dyes and
(VI) optionally up to 10% by weight of steareth-2, laureth-4 and/or ceteth-3.

Preparations of the following formulations have likewise proven to be advantageous (I) up to 12% by weight of stearic acid/palmitic acid,
(II) 0-3% by weight of cetyl alcohol, behenyl alcohol, stearyl alcohol and/or cetearyl alcohol
(III) 0.01-10% by weight of dimethicone/vinyl dimethicone crosspolymer, polysilicone-11, acrylate/alkyl acrylate crosspolymer, acrylate/vinyl isodecanoate crosspolymer, acrylate/steareth-20 methacrylate copolymer, acrylate/steareth-20 itaconate copolymer, acrylate/steareth-50 acrylate copolymer, acrylate/palmeth-25 acrylate copolymer, steareth-10 ally ether/acrylate copolymer, PEG-120 methylglucose dioleate, PEG-60 sorbitan tetraoleate, PEG-150 pentaerythrityl tetrastearte, PEG-55 propylene glycol oleate, PEG-150 distearate and/or PEG-180/laureth-50/TMMG copolymer, (IV) 0.25-1% by weight of sodium hydroxide solution and (VII) 1.0 to 5.0% by weight of pigments and/or dyes.

It may be advantageous, although it is not necessary, for the formulations according to the present invention to comprise further emulsifiers. Preference is given to using those emulsifiers which are suitable for the preparation of W/O emulsions, it being possible for these to be present either individually or else in any combinations with one another.

The further emulsifier(s) is/are advantageously chosen from the group which comprises the following compounds:

polyglyceryl-2 dipolyhydroxystearate, PEG-30 dipolyhydroxystearate, cetyldimethicone copolyol, glycol distearate, glycol dilaurate, diethylene glycoldilaurate, sorbitan trioleate, glycol oleate, glyceryl dilaurate, sorbitan tristearate, propylene glycol stearate, propylene glycol laurate, propylene glycol distearate, sucrose distearate, PEG-3 castor oil, pentaerythrityl monostearate, pentaerythrityl sesquioleate, glyceryl oleate, pentaerythrityl monooleate, sorbitan sesquioleate, isostearyl diglyceryl succinate, glyceryl caprate, palm glycerides, cholesterol, lanolin, glyceryl oleate (with 40% monoester), polyglyceryl-2 sesquiisostearate, polyglyceryl-2 sesquioleate, PEG-20 sorbitan beeswax, sorbitan oleate, sorbitan isostearate, trioleyl phosphate, glyceryl stearate and ceteareth-20 (Teginacid from Th. Goldschmidt), sorbitan stearate, PEG-7 hydrogenated castor oil, PEG-5 soy sterol, PEG-6 sorbitan beeswax, methylglucose sesquistearates, PEG-10 hydrogenated castor oil, sorbitan palmitate, PEG-22/dodecyl glycol copolymer, polyglyceryl-2 PEG-4 stearate, sorbitan laurate, PEG-4 laurate, polysorbate 61, polysorbate 81, polysorbate 65, polysorbate 80, triceteareth-4 phosphate, and sodium $C_{14-17}$ alkyl sec sulphonate (Hostacerin CG from Hoechst), polysorbate 85, trilaureth-4 phosphate, PEG-35 castor oil, sucrose stearate, trioleth-8 phosphate, $C_{12-15}$ pareth-12, PEG-40 hydrogenated castor oil, PEG-16 soy sterol, polysorbate 20, polyglyceryl-3 methylglucose distearate, PEG-40 castor oil, sodium cetearyl sulphate, lecithin, laureth-4 phosphate, propylene glycol stearate SE, PEG-25 hydrogenated castor oil, PEG-54 hydrogenated castor oil, PEG-6 caprylic/capric glycerides, glyceryl oleate and propylene glycol, polysorbate 60, polyglyceryl-3 oleate, PEG-40 sorbitan peroleate, laureth-4, isostearyl glyceryl ether, cetearyl alcohol and sodium cetearyl sulphate, PEG-22 dodecyl glycol copolymer, polyglyceryl-2 PEG-4 stearate, pentaerythrityl isostearate, polyglyceryl-3 diisostearate, sorbitan oleate and hydrogenated castor oil and Cera alba and stearic acid, sodium dihydroxycetyl phosphate and isopropyl hydroxycetyl ether, methylglucose sesquistearate, methylglucose dioleate, sorbitan oleate and PEG-2 hydrogenated castor oil and ozokerite and hydrogenated castor oil, PEG-2 hydrogenated castor oil, PEG-45/dodecyl glycol copolymer, methoxy PEG-22/dodecyl glycol copolymer, hydrogenated cocoglycerides, polyglyceryl-4 isostearate, PEG-40 sorbitan peroleate, PEG-40 sorbitan perisostearate, PEG-8 beeswax, laurylmethicone copolyol, polyglyceryl-2 laurate, stearamidopropyl PG dimonium chloride phosphate, PEG-7 hydrogenated castor oil, triethyl citrate, glyceryl stearate citrate, cetyl phosphate, polyglycerol methylglucose distearate, poloxamer 101, potassium cetyl phosphate, polyglyceryl-3 diisostearates and/or AbilCare 85 from Dow Corning.

Preferably, for the purposes of the present invention, the further emulsifier(s) is/are chosen from the group of hydrophilic emulsifiers. According to the invention, particular preference is given to mono-, di- and tri-fatty acid esters of sorbitol.

The total amount of further emulsifiers is, according to the invention, advantageously chosen to be less than 5% by weight, based on the total weight of the formulation.

The list of given further emulsifiers which can be used for the purposes of the present invention is not of course intended to be limiting.

Particularly advantageous pearlescent preparations for the purposes of the present invention are free from mono- and/or di-fatty acid esters of glycerol and/or glycol. These customarily used emulsifiers are advantageously not used in accordance with the invention in order to ensure the pearlescent effect according to the invention.

Particular preference is given to preparations according to the invention which comprise no glyceryl stearate, glyceryl isostearate, glyceryl diisostearate, glyceryl oleate, glyceryl palmitate, glyceryl myristate, glyceryl lanolate and/or glyceryl laurate.

In addition, solubility promoters may be present in the preparations, such as, for example, PEG-40 hydrogenated castor oil. The advantage of the solubility promoters is that they promote the pearlescence structures at relatively high temperatures and consequently generate an additional aesthetic benefit. As suitable solubility promoters, polysorbate 80, polysorbate 60, PEG40 castor oil, PEG-40 hydrogenated castor oil, PEG-60 hydrogenated castor oil, polyglyceryl-3 laurate, PEG-20 glyceryl laurate, methyl gluceth-20, nonoxynol-10, PPG-1 PEG-9 lauryl glycol ether, ceteth-16, PEG-16 soy sterol, PEG-10 soy sterol, C12-15 pareth-12, nonoxynol-14, octoxynol-16, PEG-20 glyceryl stearate, sorbeth-30, PPG-26 buteth-26+PEG-40 hydrogenated castor oil, tri C12-13 alkyl citrates, polyglyceryl-2 isostearates, polyglyceryl-2 diisostearates, PPG-15 stearyl ether, PEG-10 olive glycerides, PPG-3 methyl ether, PEG-2 diethyl hexanoate, C20-40 pareth-40, PEG-60 almond glycerides and/or PEG-6 caprylic/capric glycerides.

In addition, nonpolar lipids, mineral oils, silicone oils and/or waxes may be present in the cosmetic formulations in an amount up to 30% by weight, based on the total mass of the preparation.

The nonpolar lipids or waxes are preferably chosen from the group of nonpolar hydrocarbons, hydrogenated polyisobutene, cyclomethicones, dimethicones, methyl palmitate and/or dimethiconol stearate.

For the purposes of the present disclosure, the expression "lipids" is sometimes used as the generic term for fats, oils, waxes and the like, as is entirely familiar to the person skilled in the art. The terms "oil phase" and "lipid phase" are also used synonymously.

Oils and fats differ from one another, inter alia, in their polarity, which is difficult to define. It has already been proposed to adopt the interfacial tension towards water as a measure of the polarity index of an oil or of an oil phase. This means that the lower the interfacial tension between this oil phase and water, the greater the polarity of the oil phase in question. According to the invention, the interfacial tension is regarded as one possible measure of the polarity of a given oil component.

The interfacial tension is the force which acts on an imaginary line one metre in length in the interface between two phases. The physical unit for this interfacial tension is conventionally calculated from the force/length relationship and is usually expressed in mN/m (millinewtons divided by metres). It has a positive sign if it endeavours to reduce the interface. In the converse case, it has a negative sign. For the purposes of the present invention, polar lipids are regarded as being lipids whose interfacial tension towards water is less than 20 mN/m, and nonpolar lipids are regarded as being those whose interfacial tension towards water is more than 30 mN/m. Lipids with an interfacial tension towards water between 20 and 30 mN/m are generally referred to as mid-polar.

Particularly advantageous mid-polar lipids for the purposes of the present invention are the substances listed below:

| Manufacturer | Trade name | INCI name | Polarity mN/m |
| --- | --- | --- | --- |
| Stearinerie Dubois Fils | DUB VCI 10 | Isodecyl Neopentanoate | 29.9 |
| ALZO (ROVI) | Dermol IHD | Isohexyl Decanoate | 29.7 |
| ALZO (ROVI) | Dermol 108 | Isodecyl Octanoate | 29.6 |
| | Dihexyl Ether | Dihexyl Ether | 29.2 |
| ALZO (ROVI) | Dermol 109 | Isodecyl 3,5,5 Trimethyl Hexanoate | 29.1 |
| Henkel Cognis | Cetiol SN | Cetearyl Isononanoate | 28.6 |
| Unichema | Isopropyl palmitate | Isopropyl Palmitate | 28.8 |
| Dow Corning | DC Fluid 345 | Cyclomethicone | 28.5 |
| Dow Corning | Dow Corning Fluid 244 | Cyclopolydimethylsiloxane | 28.5 |
| Nikko Chemicals | Jojoba oil Gold | | 26.2 |
| Superior Jojoba Oil Gold | | | |
| Wacker | Wacker AK 100 | Dimethicone | 26.9 |
| ALZO (ROVI) | Dermol 98 | 2-Ethylhexanoic Acid 3,5,5 Trimethyl Ester | 26.2 |
| Dow Corning | Dow Corning Fluid 246 | Open | 25.3 |
| Henkel Cognis | Eutanol G | Octyldodecanol | 24.8 |
| Condea Chemie | Isofol 16 | Hexyl Decanol | 24.3 |

-continued

| Manufacturer | Trade name | INCI name | Polarity mN/m |
| --- | --- | --- | --- |
| ALZO (ROVI) | Dermol 139 | Isotridecyl 3,5,5 Trimethylhexanonanoate | 24.5 |
| Henkel Cognis | Cetiol PGL | Hexyldecanol (+) Hexyl Decyl Laurate | 24.3 |
| | Cegesoft C24 | Octyl Palmitate | 23.1 |
| Gattefossé | M.O.D. | Octyldodeceyl Myristate | 22.1 |
| | Macadamia Nut Oil | | 22.1 |
| Bayer AG, Dow Corning | Silicone oil VP 1120 | Phenyl Trimethicone | 22.7 |
| CONDEA Chemie | Isocarb 12 | Butyl Octanoic Acid | 22.1 |
| Henkel Cognis | Isopropyl stearate | Isopropyl Stearate | 21.9 |
| WITCO, Goldschmidt | Finsolv TN | C12-15 Alkyl Benzoate | 21.8 |
| Dr. Straetmans | Dermofeel BGC | Butylene Glycol Caprylate/Caprate | 21.5 |
| Unichema Huels | Miglyol 812 | Caprylic/Capric Triglyceride | 21.3 |
| Trivent (via S. Black) | Trivent OCG | Tricaprylin | 20.2 |
| ALZO (ROVI) | Dermol 866 | PEG Diethylhexanoate/ Diisononanoate/ Ethylhexyl Isononanoate | 20.1 |

Particular preference is given to nonpolar lipids. Nonpolar oils are, for example, those which are chosen from the group of branched and unbranched hydrocarbons and hydrocarbon waxes, in particular vaseline (petrolatum), paraffin oil, squalane and squalene, polyolefins and hydrogenated polyisobutenes. Among the polyolefins, polydecenes are the preferred substances.

Particularly advantageous nonpolar lipids for the purposes of the present invention are the substances listed below:

| Manufacturer | Trade name | INCI name | Polarity mN/m |
| --- | --- | --- | --- |
| Total SA | Ecolane 130 | Cycloparaffin | 49.1 |
| Neste PAD N.V. (Supplier Hansen & Rosenthal) | Nexbase 2006 FG | Polydecene | 46.7 |
| Chemische Fabrik Lehrte | Polysynlane | Hydrogenated Polyisobutene | 44.7 |
| Wacker | Wacker Silicone oil AK 50 | Polydimethylsiloxane | 46.5 |
| EC Erdölchemie (Supplier Bayer AG) | Solvent ICH | Isohexadecane | 43.8 |
| DEA Mineral oil (Supplier Hansen & Rosenthal) Tudapetrol | Pionier 2076 | Mineral Oil | 43.7 |
| DEA Mineral oil (Supplier Hansen & Rosenthal) Tudapetrol | Pionier 6301 | Mineral Oil | 43.7 |
| Wacker | Wacker Silicone oil AK 35 | Polydimethylsiloxane | 42.4 |
| EC Erdölchemie GmbH | Isoeicosane | Isoeicosane | 41.9 |
| Wacker | Wacker Silicone oil AK 20 | Polydimethylsiloxane | 40.9 |
| Condea Chemie | Isofol 1212 Carbonate | | 40.3 |
| Gattefossé | Softcutol O | Ethoxydiglycol Oleate | 40.5 |
| Creaderm | Lipodermanol OL | Decyl Olivate | 40.3 |
| Henkel | Cetiol S | Dioctylcyclohexane | 39.0 |

-continued

| Manufacturer | Trade name | INCI name | Polarity mN/m |
|---|---|---|---|
| DEA Mineral oil (Supplier Hansen & Rosenthal) Tudapetrol | Pionier 2071 | Mineral Oil | 38.3 |
| WITCO BV | Hydrobrite 1000 PO | Paraffinum Liquidum | 37.6 |
| Goldschmidt | Tegosoft HP | Isocetyl Palmitate | 36.2 |
| Condea Chemie | Isofol Ester 1693 | | 33.5 |
| Condea Chemie | Isofol Ester 1260 | | 33.0 |
| Dow Corning | Dow Corning Fluid 245 | Cyclopentasiloxane | 32.3 |
| Unichema | Prisorine 2036 | Octyl Isostearate | 31.6 |
| Henkel Cognis | Cetiol CC | Dicaprylyl Carbonate | 31.7 |
| ALZO (ROVI) | Dermol 99 | Trimethylhexyl Isononanoate | 31.1 |
| ALZO (ROVI) | Dermol 89 | 2-Ethylhexyl Isononanoate | 31.0 |
| Henkel Cognis | Cetiol OE | Dicaprylyl Ether | 30.9 |
| | Dihexyl carbonate | Dihexyl Carbonate | 30.9 |
| Albemarle S.A. | Silkflo 366 NF | Polydecene | 30.1 |
| Unichema | Estol 1540 EHC | Octyl Cocoate | 30.0 |

It is, however, also advantageous to use mixtures of high-polarity and low-polarity lipids and the like. For example, the oil phase can advantageously be chosen from the group of branched and unbranched hydrocarbons and hydrocarbon waxes, dialkyl ethers, the group of Guerbet alcohols, such as, for example, octyldodecanol, the group of saturated or unsaturated, branched or unbranched alcohols, and of fatty acid triglycerides, namely the triglycerol esters of saturated and/or unsaturated, branched and/or unbranched alkanecarboxylic acids with a chain length of from 8 to 24, in particular 12-18, carbon atoms. The fatty acid triglycerides can, for example, advantageously be chosen from the group of synthetic, semi-synthetic and natural oils, e.g. olive oil, sunflower oil, soybean oil, peanut oil, rapeseed oil, almond oil, palm oil, coconut oil, palm kernel oil and the like, provided the conditions required in the main claims are observed.

Any mixtures of oil and wax components are also to be used advantageously for the purposes of the present invention. It may also in some cases be advantageous to use waxes, for example cetyl palmitate, as the sole lipid component of the oil phase.

Fatty and/or wax components to be used advantageously according to the invention can be chosen from the group of vegetable waxes, animal waxes, mineral waxes and petrochemical waxes. Favourable according to the invention are, for example, candelilla wax, carnauba wax, japan wax, espartograss wax, suberic wax, guaruma wax, rice germ oil wax, sugar cane wax, berry wax, ouricury wax, montan wax, jojoba wax, shea butter, beeswax, shellac wax, spermaceti, lanolin (wool wax), uropygial grease, ceresin, ozokerite (earth wax), paraffin waxes and microwaxes, provided the conditions required in the main claim are observed.

Further advantageous fatty and/or wax components are chemically modified waxes and synthetic waxes, such as, for example, those available under the trade names Syncrowax HRC (glyceryl tribehenate), and Syncrowax AW 1C ($C_{18-36}$-fatty acid) from CRODA GmbH, and montan ester waxes, sasol waxes, hydrogenated jojoba waxes, synthetic or modified beeswaxes (e.g. dimethicone copolyol beeswax and/or $C_{30-50}$-alkyl beeswax), polyalkylene waxes, polyethylene glycol waxes, but also chemically modified fats, such as, for example, hydrogenated plant oils (for example hydrogenated castor oil and/or hydrogenated coconut fatty glycerides), triglycerides, such as, for example, trihydroxystearin, fatty acids, fatty acid esters and glycol esters, such as, for example, $C_{20-40}$-alkyl stearate, $C_{20-40}$-alkylhydroxystearoyl stearate and/or glycol montanate. Further advantageous are also certain organosilicon compounds which have similar physical properties to the specified fatty and/or wax components, such as, for example, stearoxytrimethylsilane.

Particularly advantageous fatty and/or wax components are chemically modified waxes and synthetic waxes, such as, for example, those available under the trade names Ultrasil IWS (dimethiconol stearate) from Noveon, and Estol 1503 (methyl palmitate) from Uniqema.

The oil phase is advantageously chosen from the group consisting of 2-ethylhexyl isostearate, octyldodecanol, isotridecyl isononanoate, butylene glycol dicaprylate/dicaprate, 2-ethylhexyl cocoate, $C_{12-15}$-alkyl benzoate, caprylic/capric triglyceride, dicaprylyl ether.

Mixtures of octyldodecanol, caprylic/capric triglyceride, dicaprylyl ether, dicaprylyl carbonate, cocoglycerides, or mixtures of $C_{12-15}$-alkyl benzoate and 2-ethylhexyl isostearate, mixtures of $C_{12-15}$-alkyl benzoate and butylene glycol dicaprylate/dicaprate and mixtures of $C_{12-15}$-alkyl benzoate, 2-ethylhexyl isostearate and isotridecyl isononanoate are particularly advantageous.

Of the hydrocarbons, paraffin oil, cycloparaffin, squalane, squalene, hydrogenated polyisobutene and polydecene are to be used advantageously for the purposes of the present invention, provided the conditions required in the main claims are observed.

It may likewise be advantageous to choose the oil phase of the preparations according to the invention in part or entirely from the group of cyclic and/or linear silicones, which are also referred to for the purposes of the present disclosure as "silicone oils". Such silicones or silicone oils may be present as monomers which are generally characterized by structural elements, as follows:

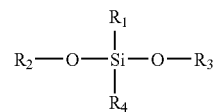

Silicone oils are high molecular weight synthetic polymeric compounds in which silicon atoms are joined in a chain-like and/or reticular manner via oxygen atoms and the remaining valences of the silicon are saturated by hydrocarbon radicals (in most cases methyl groups, less often ethyl, propyl, phenyl groups, etc.).

Linear silicones having a plurality of siloxyl units which are to be used advantageously according to the invention are generally characterized by structural elements, as follows:

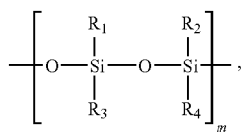

where the silicon atoms can be substituted by identical or different alkyl radicals and/or aryl radicals, which are shown here in general terms by the radicals $R_1$-$R_4$ (that is to say that the number of different radicals is not necessarily limited to 4). m can assume values from 2-200 000.

Systematically, the linear silicone oils are referred to as polyorganosiloxanes; the methyl-substituted polyorganosiloxanes, which represent the most important compounds of this group in terms of amount and are characterized by the following structural formula

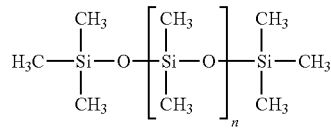

are also referred to as polydimethylsiloxane or dimethicone (INCI). Dimethicones are available in various chain lengths and with various molecular weights. Dimethicones of varying chain length and phenyltrimethicones are particularly advantageous linear silicone oils for the purposes of the present invention.

Particularly advantageous polyorganosiloxanes for the purposes of the present invention are also, for example, dimethylpolysiloxanes [poly(dimethylsiloxane)], which are available, for example, under the trade names ABIL 10 to 10 000 from Th. Goldschmidt.

Also advantageous are phenylmethylpolysiloxanes (INCI: Phenyl Dimethicone, Phenyl Trimethicone), cyclic silicones (octamethylcyclotetrasiloxane and decamethylcyclopentasiloxane), which are referred to in accordance with INCI also as cyclomethicones, amino-modified silicones (INCI: Amodimethicones) and silicone waxes, e.g. polysiloxane-polyalkylene copolymers (INCI: Stearyl Dimethicone and Cetyl Dimethicone) and dialkoxydimethylpolysiloxanes (stearoxy dimethicone and behenoxy stearyl dimethicone), which are available as various Abil-Wax grades from Th. Goldschmidt.

The silicone oils listed below are also particularly advantageous for the purposes of the present invention:

| Manufacturer | Trade name | INCI name | Polarity [mN/m] |
| --- | --- | --- | --- |
| Wacker | Wacker Silicone oil AK 100 | Polydimethylsiloxane | 26.9 |
| Wacker | Wacker Silicone oil AK 50 | Polydimethylsiloxane | 46.5 |
| Wacker | Wacker Silicone oil AK 35 | Polydimethylsiloxane | 42.4 |
| Wacker | Wacker Silicone oil AK 20 | Polydimethylsiloxane | 40.9 |
| Dow Corning | Dow Corning Fluid 245 | Cyclopentasiloxane | 32.3 |
| Dow Corning | Dow Corning Fluid 345 | Cyclomethicone | 28.5 |

Cyclic silicones to be used advantageously according to the invention are generally characterized by structural elements, as follows

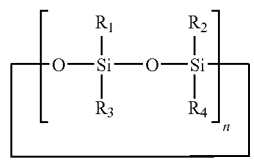

where the silicon atoms can be substituted by identical or different alkyl radicals and/or aryl radicals, which are represented here in general terms by the radicals $R_1$-$R_4$ (that is to say that the number of different radicals is not necessarily limited to 4). n can assume values from $3/2$ to 20. Fractions for n take into consideration that uneven numbers of siloxyl groups may be present in the cycle.

Particularly advantageous cyclic silicone oils for the purposes of the present invention are cyclomethicones, in particular cyclomethicones D5 and/or cyclomethicones D6.

Advantageous silicone oils or silicone waxes for the purposes of the present invention are cyclic and/or linear silicone oils and silicone waxes.

It is particularly advantageous for the purposes of the present invention to choose the ratio of lipids to silicone oils to be about 1:1 (generally x:y).

Phenyltrimethicone is advantageously chosen as silicone oil. Other silicone oils, for example dimethicone, phenyldimethicone, cyclomethicone (octamethylcyclotetrasiloxane) for example hexamethylcyclotrisiloxane, polydimethylsiloxane, poly(methylphenylsiloxane), cetyldimethicone, behenoxydimethicone are also to be used advantageously for the purposes of the present invention.

Also advantageous are mixtures of cyclomethicone and isotridecyl isononanoate, and those of cyclomethicone and 2-ethylhexyl isostearate.

It is, however, also advantageous to choose silicone oils of similar constitution to the above-described compounds whose organic side chains are derivatized, for example polyethoxylated and/or polypropoxylated. These include, for example, polysiloxane-polyalkyl-polyether copolymers, such as cetyl dimethicone copolyol, and cetyl dimethicone copolyol (and) polyglyceryl-4 isostearate (and) hexyl laurate.

Moreover, the preparations can comprise light filters, dyes, active ingredients, moisturizers, powder raw materials, fillers such as talc, silica, boron nitride and starch derivatives, preservatives and/or deodorants.

It is therefore advantageous for the purposes of the present invention to create cosmetic and dermatological preparations whose main purpose is not protection against sunlight, but which nevertheless contain UV protection substances. Thus, for example, UV-A and/or UV-B filter substances are usually incorporated into day creams or makeup products. UV protection substances, like antioxidants and, if desired, preservatives, also represent effective protection of the preparations themselves against spoilage. Also favourable are cosmetic and dermatological preparations which are present in the form of a sunscreen composition.

Accordingly, the preparations for the purposes of the present invention preferably comprise at least one UV-A and/or UV-B filter substance. The formulations may, but do not necessarily, optionally also comprise one or more organic and/or inorganic pigments as UV filter substances, which may be present in the water phase and/or the oil phase.

Preferred inorganic photoprotective filter pigments are metal oxides and/or other metal compounds which are sparingly soluble or insoluble in water, in particular oxides of titanium ($TiO_2$), zinc (ZnO), iron (e.g. $Fe_2O_3$), zirconium ($ZrO_2$), silicon ($SiO_2$), manganese (e.g. MnO), aluminium ($Al_2O_3$), cerium (e.g. $Ce_2O_3$), mixed oxides of the corresponding metals, and mixtures of such oxides, and the sulphate of barium ($BaSO_4$).

The titanium dioxide pigments may be present either in the crystal modification rutile, or else in the form of anatase and may, for the purposes of the present invention, be advantageously surface-treated ("coated"), the intention being to form or retain, for example, a hydrophilic, amphiphilic or hydrophobic character. This surface treatment can involve providing the pigments with a thin hydrophilic and/or hydrophobic inorganic and/or organic layer by processes known per se. The various surface coatings can also comprise water for the purposes of the present invention.

Described coated and uncoated titanium dioxides can also be used for the purposes of the present invention in the form of commercially available oily or aqueous predispersions. Dispersion auxiliaries and/or solubilization promoters may advantageously be added to these predispersions.

The titanium dioxides according to the invention are characterized by a primary particle size between 10 nm to 150 nm.

| Trade name | Coating | Additional constituents of the predispersion | Manufacturer |
|---|---|---|---|
| MT-100TV | Aluminium hydroxide stearic acid | — | Tayca Corporation |
| MT-100Z | Aluminium hydroxide stearic acid | — | Tayca Corporation |
| MT-100F | Stearic acid iron oxide | — | Tayca Corporation |
| MT-500SAS | Alumina, silica silicone | — | Tayca Corporation |
| MT-100AQ | Silica aluminium hydroxide alginic acid | — | Tayca Corporation |
| Eusolex T-2000 | Alumina simethicones | — | Merck KGaA |
| Eusolex TS | Alumina, stearic acid | — | Merck KGaA |
| Titanium dioxide P25 | None | — | Degussa |
| Titanium dioxide T805 (Uvinul $TiO_2$) | Octyltrimethylsilane | — | Degussa |
| UV-Titan X170 | Alumina dimethicones | — | Kemira |
| UV-Titan X161 | Alumina, silica stearic acid | — | Kemira |
| Tioveil AQ 10PG | Alumina silica | Water propylene glycol | Solaveil Uniquema |
| Mirasun TiW 60 | Alumina silica | Water | Rhone-Poulenc |

For the purposes of the present invention, particularly preferred titanium dioxides are MT-100Z and MT-100TTV from Tayca Corporation, Eusolex T-2000 and Eusolex TS from Merck and titanium dioxide T805 from Degussa.

For the purposes of the present invention, zinc oxides can also be used in the form of commercially available oily or aqueous predispersions. Zinc oxide particles suitable according to the invention and predispersions of zinc oxide particles are characterized by a primary particle size of <300 nm and are available under the following trade names from the companies listed:

| Trade name | Coating | Manufacturer |
|---|---|---|
| Z-Cote HP1 | 2% Dimethicones | BASF |
| Z-Cote | / | BASF |
| ZnO NDM | 5% Dimethicones | H&R |
| MZ 707M | 7% Dimethicones | M. Tayca Corp. |
| Nanox 500 | / | Elementis |
| ZnO Neutral | / | H&R |

Particularly preferred zinc oxides for the purposes of the invention are Z-Cote HP1 from BASF and zinc oxide NDM from Haarmann & Reimer.

The total amount of one or more inorganic pigments in the finished cosmetic preparation is advantageously chosen from the range 0.1% by weight to 25% by weight, preferably 0.5% by weight to 18% by weight.

An advantageous organic pigment for the purposes of the present invention is 2,2'-methylenebis(6-(2H-benzotriazol-2-yl)-4-(1,1,3,3-tetramethylbutyl)phenol) [INCI: Bisoctyltriazole], which is characterized by the chemical structural formula

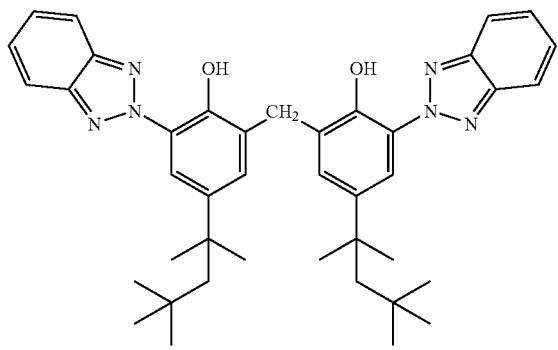

and is available under the trade name Tinosorb® M from CIBA-Chemikalien GmbH.

Advantageous UV-A filter substances for the purposes of the present invention are dibenzoylmethane derivatives, in particular 4-(tert-butyl)-4'-methoxydibenzoylmethane (CAS No. 70356-09-1), which is sold by Givaudan under the name Parsol® 1789 and by Merck under the trade name Eusolex® 9020.

Further advantageous UV-A filter substances are phenylene-1,4-bis(2-benzimidazyl)-3,3'-5,5'-tetrasulphonic acid

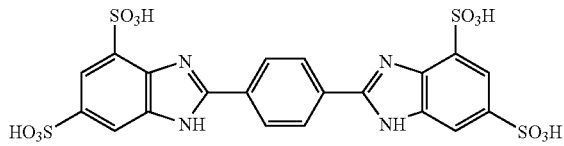

and its salts, particularly the corresponding sodium, potassium or triethanolammonium salts, in particular phenylene-1,4-bis(2-benzimidazyl)-3,3'-5,5'-tetrasulphonic bis-sodium salt

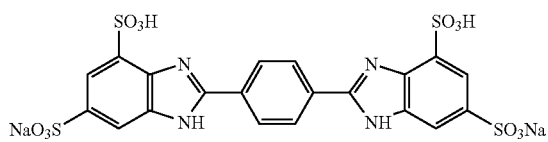

with the INCI name Bisimidazylate, which is available, for example, under the trade name Neo Heliopan AP from Haarmann & Reimer.

Also advantageous are 1,4-di(2-oxo-10-sulpho-3-bornylidenemethyl)benzene and salts thereof (in particular the corresponding 10-sulphato compounds, in particular the corresponding sodium, potassium or triethanolammonium salt), which is also referred to as benzene-1,4-di(2-oxo-3-bornylidenemethyl-10-sulphonic acid) and is characterized by the following structure:

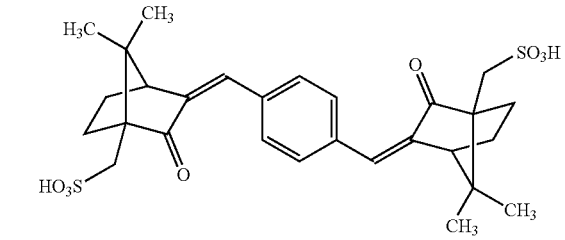

Further advantageous UV-A filter substances are hydroxybenzophenones which are characterized by the following structural formula:

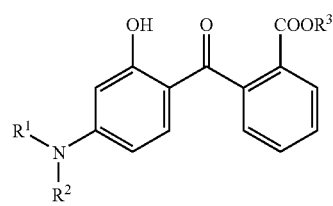

in which

R$^1$ and R$^2$, independently of one another, are hydrogen, C$_1$-C$_{20}$-alkyl, C$_3$-C$_{10}$-cycloalkyl or C$_3$-C$_{10}$-cycloalkenyl, where the substituents R$^1$ and R$^2$, together with the nitrogen atom to which they are bonded, can form a 5-membered or 6-membered ring and R$^3$ is a C$_1$-C$_{20}$-alkyl radical.

A particularly advantageous hydroxybenzophenone for the purposes of the present invention is hexyl 2-(4'-diethylamino-2'-hydroxybenzoyl)benzoate (also: aminobenzophenone), which is characterized by the following structure:

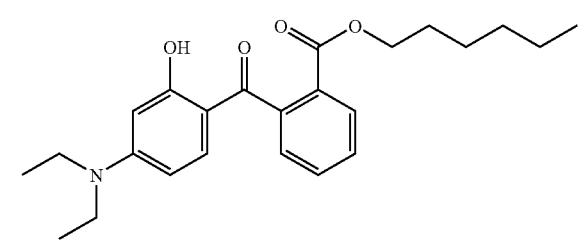

and is available under the trade name Uvinul A Plus from BASF.

Advantageous UV filter substances for the purposes of the present invention are also so-called broadband filters, i.e. filter substances which absorb both UV-A and also UV-B radiation.

Advantageous broadband filters or UV-B filter substances are, for example, bisresorcinyltriazine derivatives having the following structure:

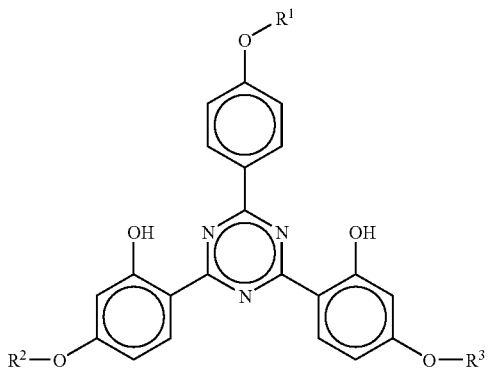

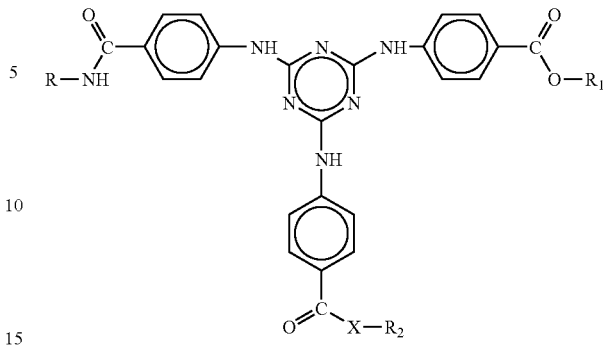

where $R^1$, $R^2$ and $R^3$, independently of one another, are chosen from the group of branched and unbranched alkyl groups having 1 to 10 carbon atoms, or are a single hydrogen atom. Particular preference is given to 2,4-bis{[4-(2-ethylhexyloxy)-2-hydroxy]-phenyl}-6-(4-methoxyphenyl)-1,3,5-triazine (INCI: Aniso Triazine), which is available under the trade name Tinosorb® S from CIBA-Chemikalien GmbH.

For the purposes of the present invention, particularly advantageous preparations which are characterized by high or very high UV-A protection preferably comprise two or more UV-A and/or broadband filters, in particular dibenzoylmethane derivatives [for example 4-(tert-butyl)-4'-methoxydibenzoylmethane], benzotriazole derivatives [for example 2,2'-methylenebis(6-(2H-benzotriazol-2-yl)-4-(1,1,3,3-tetramethylbutyl)phenol)], phenylene-1,4-bis(2-benzimidazyl)-3,3'-5,5'-tetrasulphonic acid and/or its salts, 1,4-di(2-oxo-10-sulpho-3-bornylidenemethyl)benzene and/or salts thereof and/or 2,4-bis{[4-(2-ethylhexyloxy)-2-hydroxy]phenyl}-6-(4-methoxyphenyl)-1,3,5-triazine, in each case individually or in any combinations with one another.

Other UV filter substances, which have the structural formula

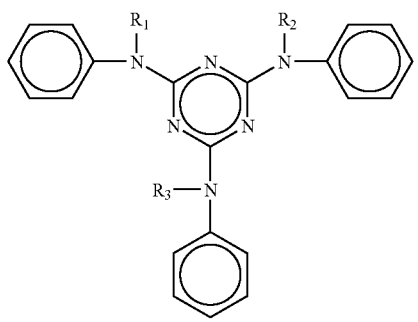

are also advantageous UV filter substances for the purposes of the present invention, for example the s-triazine derivatives described in European laid-open specification EP 570 838 A1, whose chemical structure is expressed by the generic formula where R is a branched or unbranched $C_1$-$C_{18}$-alkyl radical, a $C_5$-$C_{12}$-cycloalkyl radical, optionally substituted by one or more $C_1$-$C_4$-alkyl groups, X is an oxygen atom or an NH group, $R_1$ is a branched or unbranched $C_1$-$C_{18}$-alkyl radical, a $C_5$-$C_{12}$-cycloalkyl radical, optionally substituted by one or more $C_1$-$C_4$-alkyl groups, or a hydrogen atom, an alkali metal atom, an ammonium group or a group of the formula

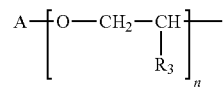

in which

A is a branched or unbranched $C_1$-$C_{18}$-alkyl radical, a $C_5$-$C_{12}$-cycloalkyl or aryl radical, optionally substituted by one or more $C_1$-$C_4$-alkyl groups, $R_3$ is a hydrogen atom or a methyl group, n is a number from 1 to 10, $R_2$ is a branched or unbranched $C_1$-$C_{18}$-alkyl radical, a $C_5$-$C_{12}$-cycloalkyl radical, optionally substituted by one or more $C_1$-$C_4$-alkyl groups, when X is the NH group, and a branched or unbranched $C_1$-$C_{18}$-alkyl radical, a $C_5$-$C_{12}$-cycloalkyl radical, optionally substituted by one or more $C_1$-$C_4$-alkyl groups, or a hydrogen atom, an alkali metal atom, an ammonium group or a group of the formula

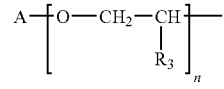

in which

A is a branched or unbranched $C_1$-$C_{18}$-alkyl radical, a $C_5$-$C_{12}$-cycloalkyl or aryl radical, optionally substituted by one or more $C_1$-$C_4$-alkyl groups, $R_3$ is a hydrogen atom or a methyl group, n is a number from 1 to 10, when X is an oxygen atom.

A particularly preferred UV filter substance for the purposes of the present invention is also an unsymmetrically substituted s-triazine, the chemical structure of which is expressed by the formula

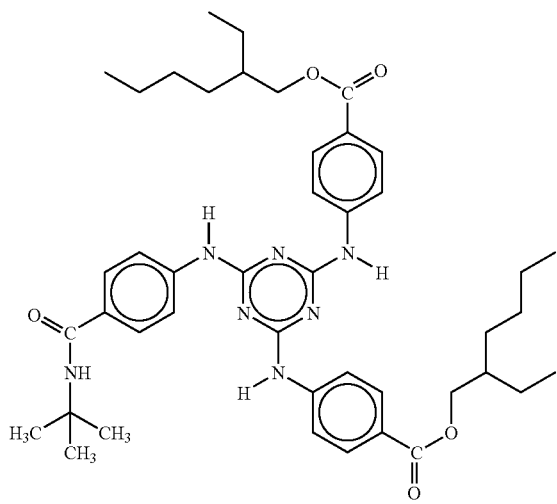

and which is also referred to below as dioctylbutylamidotriazone (INCI: Dioctylbutamidotriazone), and is available under the trade name UVASORB HEB from Sigma 3V.

Also advantageous for the purposes of the present invention is a symmetrically substituted s-triazine, tris(2-ethylhexyl) 4,4',4''-(1,3,5-triazine-2,4,6-triyltriimino)trisbenzoate, synonym: 2,4,6-tris[anilino-(p-carbo-2'-ethyl-1'-hexyloxy)]-1,3,5-triazine (INCI: Octyl Triazone), which is marketed by BASF Aktiengesellschaft under the trade name UVINUL® T 150.

European laid-open specification 775 698 also describes preferred bisresorcinyltriazine derivatives to be used, the chemical structure of which is expressed by the generic formula

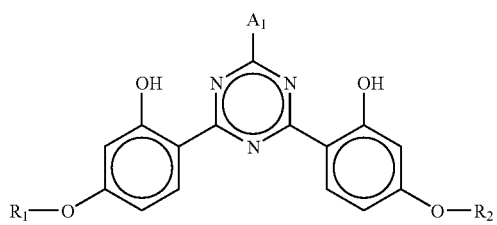

where $R_1$, $R_2$ and $A_1$ represent very different organic radicals.

Also advantageous for the purposes of the present invention are 2,4-bis{[4-(3-sulphonato)-2-hydroxypropyloxy)-2-hydroxy]phenyl}-6-(4-methoxyphenyl)-1,3,5-triazine sodium salt, 2,4-bis{[4-(3-(2-propyloxy)-2-hydroxypropyloxy)-2-hydroxy]phenyl}-6-(4-methoxyphenyl)-1,3,5-triazine, 2,4-bis{[4-(2-ethylhexyloxy)-2-hydroxy]phenyl}-6-[4-(2-methoxyethylcarboxyl)phenylamino]-1,3,5-triazine, 2,4-bis{[4-(3-(2-propyloxy)-2-hydroxypropyloxy)-2-hydroxy]phenyl}-6-[4-(2-ethylcarboxyl)phenylamino]-1,3,5-triazine, 2,4-bis{[4-(2-ethylhexyloxy)-2-hydroxy]phenyl}-6-(4-methylpyrrol-2-yl)-1,3,5-triazine, 2,4-bis{[4-tris(trimethylsiloxysilylpropyloxy)-2-hydroxy]phenyl}-6-(4-methoxyphenyl)-1,3,5-triazine, 2,4-bis{[4-(2''-methylpropenyloxy)-2-hydroxy]phenyl}-6-(4-methoxyphenyl)-1,3,5-triazine and 2,4-bis{[4-(1',1',1',3',5',5',5'-heptamethylsiloxy-2''-methylpropyloxy)-2-hydroxy]phenyl}-6-(4-methoxyphenyl)-1,3,5-triazine.

An advantageous broadband filter for the purposes of the present invention is 2,2'-methylenebis(6-(2H-benzotriazol-2-yl)-4-(1,1,3,3-tetramethylbutyl)phenol), which is characterized by the chemical structural formula

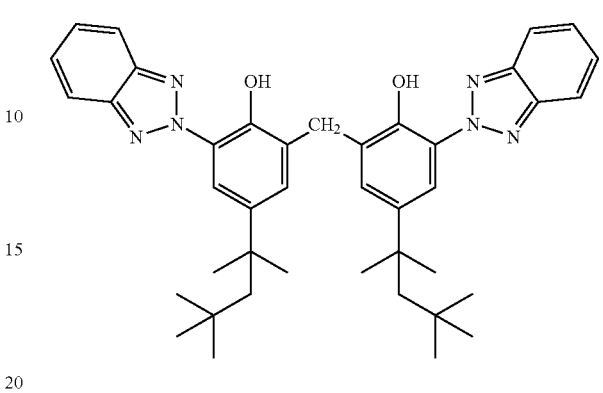

and is available under the trade name Tinosorb® M from CIBA-Chemikalien GmbH.

Another advantageous broadband filter for the purposes of the present invention is 2-(2H-benzotriazol-2-yl)-4-methyl-6-[2-methyl-3-[1,3,3,3-tetramethyl-1-[(trimethylsilyl)-oxy]disiloxanyl]propyl]phenol (CAS No.: 155633-54-8) having the INCI name Drometrizole Trisiloxane, which is characterized by the chemical structural formula

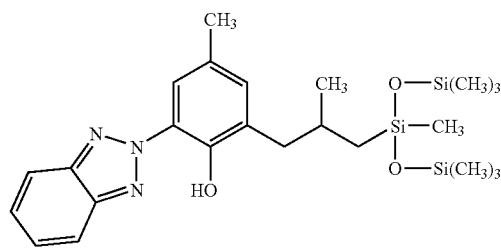

The UV-B and/or broadband filters can be oil-soluble or water-soluble. Examples of advantageous oil-soluble UV-B and/or broadband filter substances are:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate, amyl 4-(dimethylamino)benzoate;

2,4,6-trianilino(p-carbo-2'-ethyl-1'-hexyloxy)-1,3,5-triazine;

esters of benzalmalonic acid, preferably di(2-ethylhexyl) 4-methoxybenzalmalonate, esters of cinnamic acid, preferably 2-ethylhexyl 4-methoxycinnamate, isopentyl 4-methoxycinnamate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone and UV filters bonded to polymers.

Examples of advantageous water-soluble UV-B and/or broadband filter substances are:

salts of 2-phenylbenzimidazole-5-sulphonic acid, such as its sodium, potassium or its triethanolammonium salt, and also the sulphonic acid itself;

sulphonic acid derivatives of 3-benzylidenecamphor, such as, for example, 4-(2-oxo-3-bornylidenemethyl)benzenesulphonic acid, 2-methyl-5-(2-oxo-3-bornylidenemethyl)-sulphonic acid and salts thereof.

Particularly advantageous UV filter substances which are liquid at room temperature for the purposes of the present invention are homomenthyl salicylate (INCI: Homosalate), 2-ethylhexyl 2-hydroxybenzoate (2-ethylhexyl salicylate, INCI: Octyl Salicylate), 4-isopropylbenzyl salicylate and esters of cinnamic acid, preferably (2-ethylhexyl) 4-methoxycinnamate (INCI: Octyl Methoxycinnamate) and isopentyl 4-methoxycinnamate (INCI: Isoamyl p-Methoxycinnamate), 3-(4-(2,2-bisethoxycarbonylvinyl)-phenoxy)propenyl)methoxysiloxane/dimethylsiloxane copolymer (INCI: Dimethicodiethyl-benzalmalonate), which is available, for example, under the trade name Parsol® SLX from Hoffmann La Roche.

A further photoprotective filter substance which can be used advantageously according to the invention is ethylhexyl 2-cyano-3,3-diphenylacrylate (octocrylene), which is available from BASF under the name Uvinul® N 539 and is characterized by the following structure:

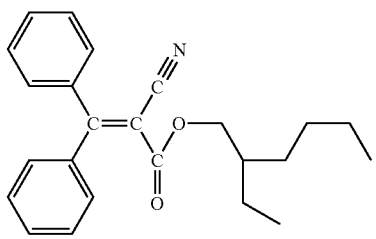

It can also be of considerable advantage to use polymer-bonded or polymeric UV filter substances in the preparations according to the present invention, in particular those described in WO-A-92/20690.

The list of specified UV filters which can be used for the purposes of the present invention is not of course intended to be limiting.

The preparations according to the invention advantageously comprise the substances which absorb UV radiation in the UV-A and/or UV-B region in a total amount of, for example, 0.1% by weight to 30% by weight, preferably 0.5 to 20% by weight, in particular 1.0 to 15.0% by weight, in each case based on the total weight of the preparations, in order to provide cosmetic preparations which protect the hair or the skin from the entire range of ultraviolet radiation. They can also be used as sunscreens for the hair or the skin.

Thus, as particular embodiments, the present invention relates to cosmetic and dermatological skincare and/or photoprotective preparations, in particular skincare or decorative cosmetic and dermatological photoprotective preparations with pearlescent effect.

The preparations according to the invention can advantageously, although not obligatorily, comprise preservatives.

Advantageous preservatives for the purposes of the present invention are, for example, formaldehyde donors (such as, for example, DMDM hydantoin, which is available, for example, under the trade name Glydant™ from Lonza), iodopropynyl butylcarbamates (e.g. those available under the trade names Glycacil-L, Glycacil-S from Lonza and/or Dekaben LMB from Jan Dekker), parabens (i.e. alkyl p-hydroxybenzoates, such as methyl-, ethyl-, propyl- and/or butylparaben), phenoxyethanol, ethanol, benzoic acid and the like. Usually, the preservative system according to the invention further advantageously also comprises preservative assistants, such as, for example, octoxyglycerol, glycine soya, etc. This list of advantageous preservatives should in no way be limiting. Instead, all preservatives approved for cosmetics or foods are advantageous for the purposes of the present invention.

Moisturizers can likewise be mixed into the cosmetic preparation. Skin moisturizing agents which can be used advantageously are glycerol, chitosan, fucogel, propylene glycol, dipropylene glycol, butylene glycol, mannitol, lactic acid, sodium pyrrolidonecarboxylic acid, hyaluronic acid, salts of the given acids, and glycine, urea and salts of metals of the first and second main group.

Glycerol, lactic acid, butylene glycol, urea, hyaluronic acid are particularly suitable.

The content of skin moisturizing agents is advantageously 3% by weight to 60% by weight, preferably 4 to 50% by weight, in particular 5 to 40% by weight, based on the total weight of the preparations.

Preparations according to the invention can advantageously also comprise powders. Powders are pulverulent preparations composed of one or more powder bases which have a greater or lesser finely divided nature and to which, depending on their intended use, one or more active ingredients, preservatives, perfume oils, dyes, etc. can be added.

The FDA's OTC Miscellaneous External Panel has stipulated the following definition for powders: "A homogeneous dispersion of finely dispersed, relatively dry finely divided material which consists of one or more substances" (FDC Reports [Pink Sheet] 41, No. 33, T&G-4 [Aug. 13, 1979]).

The composition of a powder depends largely on the objectives which it has to fulfil. Powders can, however, also be diluents for medicaments, e.g. antibiotics, sulphonamides, etc. Liquid powders are mostly high-viscosity preparations (lotions) consisting of talc, zinc oxide and/or titanium dioxide, glycerol and water. Compact powders are powder bases briquetted by high pressure or caked together by adding calcium sulphate (gypsum).

Additionally, powders are also provided and used in aerosol form after it was possible to develop valves which largely exclude the possibility of the valve execution operations being obstructed.

The sedimentation of the incorporated powder particles, which is always a risk, can likewise be prevented by incorporating suitable suspending agents and/or suspension auxiliaries into the formulation, for example alkali metal, ammonium or amine salts of a dialkyl sulphosuccinate with alkyl groups of 4-12 carbon atoms, e.g. sodium dioctyl sulphosuccinate (typically about 0.002-0.015% by weight), or an alkylbenzenesulphonic acid with alkyl groups of 8-14 carbon atoms, e.g. sodium dodecylbenzenesulphonate.

Depending on the field of use, customary cosmetic fillers, additives, perfumes and also care substances and active ingredients can be incorporated into the preparations according to the invention. In formulations according to the invention it is possible to incorporate both large amounts of hydrophilic and also hydrophobic active ingredients or combinations of hydrophilic and hydrophobic active ingredients into the formulations. Such active ingredients advantageous according to the invention are, for example, acetylsalicylic acid, azulene, ascorbic acid (vitamin C), vitamin $B_1$, vitamin $B_{12}$, vitamin $D_1$, but also bisabolol, unsaturated fatty acids, namely the essential fatty acids (often also called vitamin F), in particular γ-linolenic acid, oleic acid, eicosapentaenoic acid, docosahexaenoic acid, camphor, extracts or other products of vegetable and animal origin, e.g. evening primrose oil, borage oil or currant seed oil, fish oils, cod liver oil or else ceramides and ceramide-like compounds and so on.

In addition, it is possible to incorporate care active ingredients which are not limited to the fat-soluble active ingredients, but can also be chosen from the group of water-soluble active ingredients, for example vitamins and the like.

A surprising property of the preparations according to the invention is that they are very good vehicles for cosmetic or dermatological active ingredients into the skin, preferred active ingredients being antioxidants which can protect the skin against oxidative stress.

It is in some cases possible and advantageous to use the preparations according to the invention as bases for pharmaceutical formulations. Corresponding requirements apply mutatis mutandis to the formulation of medicinal preparations. The transitions between pure cosmetics and pure pharmaceuticals are fluid here. Suitable pharmaceutical active ingredients according to the invention are in principle all classes of active ingredient, preference being given to lipophilic active ingredients. Examples are: antihistamines, antiphlogistics, antibiotics, antimycotics, active ingredients which promote circulation, keratolytics, hormones, steroids, vitamins, etc.

By using amphiphilic polymers and/or associative polymers and/or siloxane elastomers (III) it is now possible for the first time to formulate emulsions with long-term stability and with cosmetic pearlescence optics which have significantly improved skin compatibility in stearate systems even when NaOH is used as the sole base for neutralization.

By virtue of the preparations according to the invention, it is additionally possible for the first time to formulate pearlescent emulsions which have a high content of lipids, including ones of varying polarity and waxes up to a content of 30% by weight, have long-term stability, significantly improve the sensory properties of the hitherto very dull and sticky pearlescence systems, have supple, soft, nonsticky, cosmetically sliding properties, have a fatty acid content of less than 12% by weight with a hydrolysed fraction of a maximum of 9% by weight, have significantly improved skin compatibility can comprise an increased fatty alcohol content of up to 10% by weight without impairing crystal formation and thus the pearlescence optics.

A preferred way of forming emulsions according to the invention consists in immobilizing the oil droplets through the use of hydrophobically modified, synthetic or natural polymers. Such polymers are sometimes also referred to as associative thickeners. Associative polymers include crosslinker substances, for the purposes of the present description also referred to as thickeners, which form an independent gel network in which the emulsion droplets are then held by hydrophobic interaction. So-called associative and/or amphiphilic thickeners are thus then present. The network can also be held together here by the crosslinking with the emulsion droplets at the points of intersection in the network.

The invention further provides the use of the preparation as cosmetics for achieving an optically pleasing pearlescent effect. The preparations can be used and administered in the form of a cream, lotion, foams, spray. Moreover, the preparations according to the invention can be used as decorative cosmetics, makeup, whitening products, cooling products, sunscreens and, in particular, as face-care, bodycare and handcare products.

DETAILED DESCRIPTION OF THE INVENTION

Examples

| Example | 1 | 2 | 3 | 4 | 5 | 6 | 7 | 8 |
|---|---|---|---|---|---|---|---|---|
| Stearic acid/palmitic acid | 6.0 | 4.5 | 7.5 | 5.0 | 7.5 | 4.5 | 5.0 | 4.5 |
| PEG-20 stearate | | 1.5 | | | | | 0.5 | |
| PEG-40 stearate | 2.0 | | | 0.5 | 1.5 | 1.5 | | 4.5 |
| PEG-100 stearate | | | 2.5 | 1.0 | 1.0 | | 0.5 | |
| Steareth-2 | | 0.5 | | | 0.5 | | 0.6 | |
| Laureth-4 | 1.0 | | | 0.5 | | 0.6 | 0.2 | 0.5 |
| Ceteth-4 | | | 0.2 | | | 0.4 | | |
| Cetyl alcohol | 2.0 | | | 1.5 | | | 1.0 | |
| Behenyl alcohol | | 1.5 | | | | | | |
| Stearyl alcohol | | | 1.0 | | 2.5 | 0.5 | | |
| Cetearyl alcohol | | 1.5 | | | | 1.0 | | 1.5 |
| Cetyl palmitate | | | | 1.0 | | | | |
| Myristyl myristate | | 1.0 | | | | | 1.0 | |
| Dimethiconol stearate | 2.0 | | | | 4.0 | | | |
| Hydrogenated cocoglyceride | | | 1.0 | | 0.5 | | | |
| Shea butter | | 1.0 | | | | | 0.5 | |
| Silicone waxes (e.g. Abil Wax 9840) | | | 2.0 | | | | | |
| Methyl palmitate | | | | 1.0 | | | 3.0 | |
| C12-15 alkyl benzoate | | | 3.0 | 3.0 | | | | |
| Butylene glycol dicaprylate/dicaprate | | | | 1.0 | | | | |
| Caprylic/capric triglyceride | | | | | | | | 1.0 |
| Ethylhexyl cocoate | | | | | | | | 2.0 |
| Octyldodecanol | | 3.0 | | | | | 3.0 | |
| Mineral oil | | 2.0 | 1.0 | | | | | |
| Hydrogenated polyisobutene | 5.0 | | | | | 4.0 | | |
| Polydecene | | 2.0 | | | 2.0 | | 1.0 | |
| Petrolatum | | | 2.0 | | 2.0 | | | |
| Cyclomethicone | 5.0 | 2.0 | 1.0 | 2.0 | | 4.0 | | 8.0 |
| Dimethicone | 1.0 | 3.0 | | 2.0 | 2.0 | 2.0 | 1.0 | 2.0 |
| Phenyltrimethicone | | | 1.0 | | | 1.0 | | |

| -continued | | | | | | | |
|---|---|---|---|---|---|---|---|
| Dicaprylyl ether | | | 2.5 | | | | |
| Dicaprylyl carbonate | | | | | 3.0 | | |
| Natural oils (e.g. triglycerides such as jojoba oil) | 0.5 | | | 1.0 | | | |
| Siloxane elastomers (such as e.g. dimethicone/vinyl dimethicone crosspolymer; Dow Corning 9506 powder or Polysilicone-11, Gransil GCM-5) | | 1.0 | 2.0 | | 4.0 | | |
| Hydrophobically modified acrylates - amphiphilic polymers such as e.g. acrylate/alkyl acrylate crosspolymer, acrylate/vinyl isodecanoate crosspolymer | 0.5 | 0.5 | | 0.25 | | 0.5 | 0.5 |
| Associative polymers of the HASE type, (such as e.g. acrylate/steareth-20 methacrylate copolymer, acrylate/steareth-20 itaconate copolymer, acrylate/steareth-50 acrylate copolymer, acrylate/palmeth-25 acrylate copolymer, steareth-10 allyl ether/acrylate copolymer) | | | 0.5 | | 0.1 | | |
| Associative polymers of the hydrophobically modified POE copolymer type (such as e.g. PEG-120 methylglucose dioleate, PEG-60 sorbitan tetraoleate, PEG-150 pentaerythrityl tetrastearate, PEG-55 propylene glycol oleate, PEG-150 distearate, PEG-180/laureth-50/TMMG copolymer) | | 0.1 | 0.1 | 0.25 | 0.5 | | 0.5 |
| Trisodium EDTA | 0.2 | 0.1 | | 0.05 | | 0.1 | 0.3 |
| Iminodisuccinate | 0.1 | | 0.1 | | 0.3 | | 0.5 |
| Phenoxyethanol | 0.3 | 0.1 | | 0.5 | 0.8 | | 0.4 |
| Parabens | 0.6 | | 0.4 | | 0.4 | 0.2 | |
| Hexamidine diisethionate | | 0.1 | | | 0.05 | 0.1 | |
| Imidodiazolydynlurea | | | | | 0.2 | | 0.2 |
| DMDM hydantoin | | | 0.2 | | | 0.1 | |
| Iodopropynyl butylcarbamate | | | | 0.2 | | 0.05 | |
| Alcohol denat. | 5.0 | | 2.0 | | 10.0 | | 8.0 |
| Octoxyglycerol | | 1.0 | | | 3.0 | 5.0 | |
| Xanthan gum | | | | | 0.1 | | |
| Carbomer | 0.05 | | | | | 0.2 | |
| Polyacrylamide | | | 0.2 | | | | 0.2 |
| Cellulose ether | | | | | | 0.1 | |
| C18-36 acid triglyceride | | | | 0.2 | | | |
| PVP/hexadecene copolymer | | | | 0.1 | | | |
| Tricontayl PVP | | | | | | 0.1 | |
| Hydroxypropylcellulose | | | 0.05 | | | | |
| Phenylbenzimidazole-sulphonic acid | | | | | | 2.0 | |
| Bisethylhexyloxyphenol methoxyphenyltriazine | | | | 1.0 | | | |
| Ethylhexyltriazone | | | | 0.5 | | | |
| Butyl methoxydibenzoyl-methane | | | | 1.0 | | | |
| Disodium phenyldi-benzimidazoletetrasulphonate | | | | | | 1.0 | |
| Titanium dioxide T 805 | | | 0.50 | | | 0.50 | 0.50 |
| Ethylhexyl methoxycinnamate | | | | 2.0 | | | 4.0 |
| Octocrylene | | | 1.5 | | | | |
| Benzophenone-3 | | | 1.5 | | | | |
| Fillers (distarch phosphate, tapioca starch, aluminium starch octenyl succinate, silica, talc, boron nitride) | | 2.0 | 4.0 | | 3.0 | | |
| Pigments and/or dyes, pearlescent pigments based on coated mica (such as Timiron, from Merck), or coated SiO$_2$ particles ("rona-spheres") or coated aluminium | 1.0 | 2.0 | 5.0 | 0.5 | 2.5 | 10.0 | 0.1 | 1.5 |

-continued

| | | | | | | | | |
|---|---|---|---|---|---|---|---|---|
| oxide particles (such as Xirona from Merck) | | | | | | | | |
| Perfume | q.s. | q.s. | q.s. | q.s. | q.s. | q.s. | q.s. | q.s. |
| Sodium and/or potassium hydroxide solution | q.s. | q.s. | q.s. | q.s. | q.s. | q.s. | q.s. | q.s. |
| Aqua | ad. 100 | ad. 100 | ad. 100 | ad. 100 | ad. 100 | ad. 100 | ad. 100 | ad. 100 |

| Examples | 9 | 10 | 11 | 12 | 13 | 14 | 15 | 16 |
|---|---|---|---|---|---|---|---|---|
| Stearic acid/palmitic acid | 10.0 | 10.0 | 7.5 | 6.0 | 10.0 | 8.5 | 10.0 | 10.0 |
| Cetyl alcohol | 0.5 | | | | | | 0.5 | |
| Behenyl alcohol | | | 0.5 | | | | | |
| Stearyl alcohol | | | | | 0.25 | | | |
| Cetearyl alcohol | | 0.25 | | | | | | 0.5 |
| Cetyl palmitate | | | | 1.0 | | | | |
| Myristyl myristate | | 1.0 | | | | | | |
| Dimethiconol stearate | 1.0 | | | | | | | |
| Hydrogenated cocoglyceride | | | 1.0 | | 0.5 | | | |
| Shea butter | | 1.0 | | | | | 0.5 | |
| Silicone waxes (e.g. Abil Wax 9840) | | | 2.0 | | | | | |
| Methyl palmitate | 5.0 | 10.0 | 20.0 | 5.0 | 5.0 | 10.0 | 10.0 | 5.0 |
| C12-15 alkyl benzoate | | | 3.0 | 3.0 | | | | |
| Butylene glycol dicaprylate/dicaprate | | | | 1.0 | | | | |
| Caprylic/capric triglyceride | | | | | | | | 1.0 |
| Ethylhexyl cocoate | | | | | | | | 2.0 |
| Octyldodecanol | | 3.0 | | | | | 3.0 | |
| Mineral oil | | | 1.0 | | | | | |
| Hydrogenated polyisobutene | | | | | | 2.5 | | |
| Polydecene | | | | 2.0 | | | 1.0 | |
| Petrolatum | | | 2.0 | | 2.0 | | | |
| Cyclomethicone | 5.0 | 2.0 | 1.0 | 2.0 | | 4.0 | 5.0 | 8.0 |
| Dimethicone | 1.0 | 3.0 | | 2.0 | 5.0 | 2.0 | 1.0 | 2.0 |
| Phenyltrimethicone | | | 1.0 | | | 1.0 | | |
| Dicaprylyl ether | | | 1.0 | | | | | |
| Dicaprylyl carbonate | | | | | 3.0 | | | |
| Natural oils (e.g. triglycerides such as jojoba oil) | 0.5 | | | 1.0 | | | | |
| Siloxane elastomers (such as e.g. dimethicone/vinyl dimethicone crosspolymer; Dow Corning 9506 powder or Polysilicone-11, Gransil GCM-5) | | | 2.0 | | 4.0 | | | |
| Hydrophobically modified acrylates - amphiphilic polymers such as e.g. acrylate/alkyl acrylate crosspolymer, acrylate/vinyl isodecanoate crosspolymer | | | | | | 0.1 | 0.1 | |
| Associative polymers of the HASE type (such as e.g. acrylate/steareth-20 methacrylate copolymer, acrylate/steareth-20 itaconate copolymer, acrylate/steareth-50 acrylate copolymer, acrylate/palmeth-25 acrylate copolymer, steareth-10 allyl ether/acrylate copolymer) | 0.5 | 0.5 | 0.5 | 0.25 | | 0.5 | | 0.5 |
| Associative polymers of the hydrophobically modified POE copolymer type (such as e.g. PEG-120 methyl-glucose dioleate, PEG-60 sorbitan tetraoleate, PEG-150 pentaerythrityl tetrastearate, PEG-55 propylene glycol oleate, PEG-150 distearate, PEG-180/laureth-50/TMMG copolymer) | | 0.1 | 0.1 | 0.25 | 0.5 | | 0.5 | |
| Trisodium EDTA | 0.2 | 0.1 | | 0.05 | | 0.1 | 0.3 | |
| Iminodisuccinate | 0.1 | | 0.1 | | 0.3 | | | 0.5 |
| Phenoxyethanol | 0.3 | 0.1 | | 0.5 | 0.8 | | | 0.4 |
| Parabens | 0.6 | | 0.4 | | 0.4 | | 0.2 | |

-continued

| | | | | | | | | |
|---|---|---|---|---|---|---|---|---|
| Hexamidine diisethionate | | 0.1 | | | 0.05 | | 0.1 | |
| Imidodiazolydynlurea | | | | | | 0.2 | | 0.2 |
| DMDM hydantoin | | | 0.2 | | | 0.1 | | |
| Iodopropynyl butylcarbamate | | | | 0.2 | | | 0.05 | |
| Alcohol denat. | 5.0 | | 2.0 | | | 10.0 | | 8.0 |
| Octoxyglycerol | | 1.0 | | | 3.0 | | 5.0 | |
| Xanthan gum | | | | | 0.1 | | | |
| Carbomer | 0.05 | | | | | 0.2 | | |
| Polyacrylamide | | | 0.2 | | | | | 0.2 |
| Cellulose ether | | | | | | | 0.1 | |
| C18-36 acid triglyceride | | | | 0.2 | | | | |
| PVP/hexadecene copolymer | | | 0.1 | | | | | |
| Tricontayl PVP | | | | | | 0.1 | | |
| Hydroxypropylcellulose | | | 0.05 | | | | | |
| Phenylbenzimidazole-sulphonic acid | | | | | | | 1.0 | |
| Bisethylhexyloxyphenol methoxyphenyltriazine | | | | 1.0 | | | | |
| Ethylhexyltriazone | | | | 0.5 | | | | |
| Butyl methoxydibenzoyl-methane | | | | 1.0 | | | | |
| Disodium phenyldi-benzimidazoletetra-sulphonate | | | | | | | 1.0 | |
| Titanium dioxide T 805 | | | 1.0 | | | 0.50 | 1.0 | |
| Ethylhexyl methoxy-cinnamate | | | | 2.0 | | | 4.0 | |
| Octocrylene | | | 2.0 | | | | | |
| Benzophenone-3 | | | 2.0 | | | | | |
| Fillers (distarch phosphate, tapioca starch, aluminium starch octenyl succinate, silica, talc, boron nitride) | | 2.0 | 4.0 | | | 3.0 | | |
| Pigments and/or dyes, such as e.g. pearlescent pigments based on coated mica (such as Timiron, from Merck), coated SiO$_2$ particles ("ronaspheres"), coated aluminium oxide particles (such as Xirona from Merck) | 1.0 | 2.0 | 5.0 | 0.5 | 2.5 | 10.0 | 0.1 | 1.5 |
| Perfume | q.s. | q.s. | q.s. | q.s. | q.s. | q.s. | q.s. | q.s. |
| Sodium and/or potassium hydroxide solution | q.s. | q.s. | q.s. | q.s. | q.s. | q.s. | q.s. | q.s. |
| Water | ad. 100 | ad. 100 | ad. 100 | ad. 100 | ad. 100 | ad. 100 | ad. 100 | ad. 100 |

All of the example formulations listed produce an extraordinarily stable emulsion with pearlescence optics. In contrast to the pearlescent emulsions of the prior art, they are characterized by very good skincare properties, good skin compatibility and sensorially balanced cosmetic properties.

In particular, the significantly marked optical effects (pearlescence & shimmer) give the photoprotective and/or skincare products on the one hand a luxurious, expensive, valuable, new type of impression and a completely new type of appearance for skincare products according to current prior art. At the same time, such cosmetic and/or dermatological preparations additionally give the consumer an indication of the effects achieved on the skin upon use.

What is claimed is:

1. A cosmetic or dermatological composition, wherein the composition is pearlescent, is substantially free of mono- and di-fatty acid esters of glycerol and glycol, and comprises:
   (I) up to 10% by weight of at least one of stearic acid, isostearic acid, myrisitic acid, and palmitic acid,
   (II) from 0.1% to 10% by weight of at least one of myristyl alcohol, cetyl alcohol, behenyl alcohol, stearyl alcohol, and cetearyl alcohol,
   (III) from 0.01% to 10% by weight of at least one of dimethicone/vinyl dimethicone crosspolymer, polysilicone-11, acrylate/alkyl acrylate crosspolymer, acrylate/vinyl isodecanoate crosspolymer, acrylate/steareth-20 methacrylate copolymer, acrylate/steareth-20 itaconate copolymer, acrylate/steareth-50 acrylate copolymer, acrylate/palmeth-25 acrylate copolymer, steareth-10 alkyl ether/acrylate copolymer, PEG-120 methylglucose dioleate, PEG-60 sorbitan tetraoleate, PEG-150 pentaerythrityl tetrastearate, PEG-55 propylene glycol oleate, PEG-150 distearate and PEG-180/laureth-50/TMMG copolymer, PEG-180/octoxynol-40/tetramethoxymethylglycoluril copolymer, PEG-180/laureth-50/tetramethoxymethylglycoluril copolymer, PEG-150 dioleate, PEG-300 pentaerythrityl tetraisostearate, PEG-160 sorbitan triisostearate, PEG-450 sorbitol hexaisostearate, PEG-230 glyceryl triisostearate, cetylhydroxyethylcellulose, polyquaternium-24, lauryl dimethicone/vinyldimethicone crosspolymer, and cyclomethicone vinyldimethicone/methicone crosspolymer, (IV) sodium hydroxide as neutralizing agent, (V) up to 10% by weight of at least one of PEG-20 stearate, PEG-40 stearate, PEG-100 stearate, PEG-9 stearate, PEG-8 distearate, PEG-8 stearate, PEG-8 oleate, PEG-25 glyceryl trioleate, PEG-40 sorbitan lanolate, PEG-15 glyceryl ricinoleate, PEG-20 glyceryl stearate, PEG-20 glyceryl isostearate, PEG-20 glyceryl oleate, PEG-20 methylglucose sesquistearate, PEG-30 glyceryl isostearate, PEG-20 glyceryl laurate, PEG-30 stearate, PEG-30 glyceryl stearate, PEG-30 glyceryl laurate, PEG-50 stearate, and PEG-150 laurate, (VI) from 0% to 10% by weight of at least one of steareth-2, laureth-4, ceteth-3, ceteareth-3, ceteareth-6, steareth-2, steareth-10, ceteth-10, isosteareth-10, laureth-2, laureth-3, laureth-4, myreth-4, laneth-5, ceteth-2, oleth-2, oleth-3, and oleth-5, and (VII) from 0.1% to 30% by weight of at least one of a pigment and a dye comprising at least one of coated mica particles, $TiO_2$ particles, $Fe_2O_3$ particles, zinc oxide-coated $SiO_2$ particles, iron pearlescent pigments prepared without the use of mica, and aluminum pearlescent pigments.

2. The composition of claim 1, wherein (I) comprises at least one of stearic acid and palmitic acid.

3. The composition of claim 1, wherein (III) comprises at least one of dimethicone/vinyl dimethicone crosspolymer, polysilicone-11, acrylate/alkyl acrylate crosspolymer, acrylate/vinyl isodecanoate crosspolymer, acrylate/steareth-20 methacrylate copolymer, acrylate/steareth-20 itaconate copolymer, acrylate/steareth-50 acrylate copolymer, acrylate/palmeth-25 acrylate copolymer, steareth-10 allyl ether/acrylate copolymer, PEG-120 methylglucose dioleate, PEG-60 sorbitan tetraoleate, PEG-150 pentaerythrityl tetrastearate, PEG-55 propylene glycol oleate, PEG-150 distearate, and PEG-180/laureth-50/TMMG copolymer.

4. The composition of claim 1, wherein (III) comprises at least one of an acrylate/alkyl acrylate crosspolymer and an acrylate/vinyl isodecanoate crosspolymer.

5. The composition of claim 1, wherein (III) comprises at least one of acrylate/steareth-20 methacrylate copolymer, acrylate/steareth-20 itaconate copolymer, acrylate/steareth-50 acrylate copolymer, acrylate/palmeth-25 acrylate copolymer and steareth-10 allyl ether/acrylate copolymer.

6. The composition of claim 1, wherein (III) comprises at least one of PEG-120 methylglucose dioleate, PEG-60 sorbitan tetraoleate, PEG-150 pentaerythrityl tetra-stearate, PEG-55 propylene glycol oleate, PEG-150 distearate and PEG-180/laureth-50/TMMG copolymer.

7. The composition of claim 1, wherein (III) comprises at least one of dimethicone/vinyl dimethicone crosspolymer and polysilicone-11.

8. The composition of claim 1, wherein (V) comprises at least one of PEG-30 stearate, PEG-40 stearate and PEG-100 stearate.

9. The composition of claim 1, wherein (VI) comprises at least one of steareth-2, laureth-4 and ceteth-3.

10. The composition of claim 1, wherein a ratio (I):(II):(V) is from 5:1:1 to 1:1:5.

11. The composition of claim 1, wherein a ratio (I):(II):(V) is from 3:1:1 to 3:1:3.

12. The composition of claim 1, wherein a ratio (I):(II):(V) is from 3:1:1 to 1:1:3.

13. The composition of claim 1, wherein the composition comprises from 0.5% to 15% by weight of (VII).

14. The composition of claim 1, wherein the composition comprises from 0.1% to 10% by weight of (I).

15. The composition of claim 1, wherein the composition comprises from 0.1% to 5% by weight of (II).

16. The composition of claim 1, wherein the composition comprises up to 3% by weight of (II).

17. The composition of claim 1, wherein the composition comprises up to 5% by weight of (V).

18. The composition of claim 1, wherein the composition comprises from 0.01% to 5% by weight of at least one of an amphiphilic polymer and an associative polymer selected from (III).

19. The composition of claim 1, wherein the composition comprises from 0.1% to 1% by weight of at least one of an amphiphilic polymer and an associative polymer selected from (III).

20. The composition of claim 1, wherein the composition comprises at least 0.5% by weight of a siloxane elastomer selected from (III).

21. The composition of claim 1, wherein the composition comprises from 0.15% to 1% by weight of (IV).

22. The composition of claim 1, wherein the composition comprises sodium hydroxide as the only neutralizing agent.

23. The composition of claim 1, wherein (VI) comprises laureth-4.

24. The composition of claim 1, wherein not more than 9% of (I) is saponified.

25. The composition of claim 1, wherein the composition further comprises PEG-40 hydrogenated castor oil.

26. The composition of claim 1, wherein the composition further comprises ethanol in an amount of up to 30% by weight.

27. A decorative cosmetic product which comprises the composition of claim 1.

28. A skin care product which comprises the composition of claim 1.

29. A photoprotective product which comprises the composition of claim 1.

30. A cleansing emulsion which comprises the composition of claim 1.

31. A cosmetic or dermatological composition, wherein the composition is pearlescent, is substantially free of mono- and di-fatty acid esters of glycerol and glycol, and comprises:

(I) up to 10% by weight of at least one of stearic acid and palmitic acid, (II) from 0.1% to 10% by weight of at least one of cetyl alcohol, behenyl alcohol, stearyl alcohol and cetearyl alcohol, (III) from 0.01% to 10% by weight of at least one of dimethicone/vinyl dimethicone crosspolymer, polysilicone-11, acrylate/alkyl acrylate crosspolymer, acrylate/vinyl isodecanoate crosspolymer, acrylate/steareth-20 methacrylate copolymer, acrylate/steareth-20 itaconate copolymer, acrylate/steareth-50 acrylate copolymer, acrylate/palmeth-25 acrylate copolymer, steareth-10 alkyl ether/acrylate copolymer, PEG-120 methylglucose dioleate, PEG-60 sorbitan tetraoleate, PEG-150 pentaerythrityl tetrastearate, PEG-55 propylene glycol oleate, PEG-150 distearate, and PEG-180/laureth-50/TMMG copolymer, (IV) from 0.15% to 1% by weight of sodium hydroxide as neutralizing agent, (V) up to 10% by weight of at least one of PEG-20 stearate, PEG-40 stearate and PEG-100 stearate, (VI) from 0% to 10% by weight of at least one of steareth-2, laureth-4 and ceteth-3, and (VII) from 1.0% to 5.0% by weight of at least one of a pigment and a dye comprising at least one of coated mica particles, TiO particles, $Fe_2O_3$ particles, zinc oxide-coated $SiO_2$ particles, iron pearlescent pigments prepared without the use of mica, and aluminum pearlescent pigments.

32. The composition of claim 31, wherein (III) comprises at least one of an acrylate/alkyl acrylate crosspolymer and an acrylate/vinyl isodecanoate crosspolymer.

33. The composition of claim 31, wherein (III) comprises at least one of acrylate/steareth-20 methacrylate copolymer, acrylate/steareth-20 itaconate copolymer, acrylate/steareth-50 acrylate copolymer, acrylate/palmeth-25 acrylate copolymer and steareth-10 alkyl ether/acrylate copolymer.

34. The composition of claim 31, wherein (III) comprises at least one of PEG-120 methylglucose dioleate, PEG-60 sorbitan tetraoleate, PEG-150 pentaerythrityl tetra-stearate, PEG-55 propylene glycol oleate, PEG-150 distearate and PEG-180/laureth-50/TMMG copolymer.

35. The composition of claim 31, wherein (III) comprises at least one of dimethicone/vinyl dimethicone crosspolymer and polysilicone-11.

36. The composition of claim 31, wherein a ratio (I):(II):(V) is from 5:1:1 to 1:1:5.

37. The composition of claim 31, wherein a ratio (I):(II):(V) is from 3:1:1 to 3:1:3.

38. The composition of claim 31, wherein a ratio (I):(II):(V) is from 3:1:1 to 1:1:3.

39. The composition of claim 31, wherein the composition comprises from 0.1% to 5% by weight of (II).

40. The composition of claim 31, wherein the composition comprises up to 3% by weight of (II).

41. The composition of claim 31, wherein the composition comprises up to 5% by weight of (V).

42. The composition of claim 31, wherein the composition comprises from 0.01% to 5% by weight of at least one of an amphiphilic polymer and an associative polymer selected from (III).

43. The composition of claim 31, wherein the composition comprises from 0.1% to 1% by weight of at least one of an amphiphilic polymer and an associative polymers polymer selected from (III).

44. The composition of claim 31, wherein the composition comprises at least 0.5% by weight of a siloxane elastomer selected from (III).

45. The composition of claim 31, wherein the composition comprises from 0.15% to 1% by weight of (IV).

46. The composition of claim 31, wherein the composition comprises sodium hydroxide as the only neutralizing agent.

47. The composition of claim 31, wherein (VI) comprises laureth-4.

48. The composition of claim 31, wherein not more than 9% of (I) is saponified.

49. The composition of claim 31, wherein the composition further comprises PEG-40 hydrogenated castor oil.

50. The composition of claim 31, wherein the composition further comprises ethanol in an amount of up to 30% by weight.

51. A decorative cosmetic product which comprises the composition of claim 31.

52. A skin care product which comprises the composition of claim 31.

53. A photoprotective product which comprises the composition of claim 31.

54. A cleansing emulsion which comprises the composition of claim 31.

55. A cosmetic or dermatological composition, wherein the composition is pearlescent, is substantially free of mono- and di-fatty acid esters of glycerol and glycol, and comprises:
  (I) up to 10% by weight of at least one of stearic acid and palmitic acid,
  (II) from 0.1% to 5% by weight of at least one of cetyl alcohol, behenyl alcohol, stearyl alcohol and cetearyl alcohol,
  (III) from 0.01% to 10% by weight of at least one of dimethicone/vinyl dimethicone crosspolymer, polysilicone-11, acrylate/alkyl acrylate crosspolymer, acrylate/vinyl isodecanoate crosspolymer, acrylate/steareth-20 methacrylate copolymer, acrylate/steareth-20 itaconate copolymer, acrylate/steareth-50 acrylate copolymer, acrylate/palmeth-25 acrylate copolymer, steareth-10 alkyl ether/acrylate copolymer, PEG-120 methylglucose dioleate, PEG-60 sorbitan tetraoleate, PEG-150 pentaerythrityl tetrastearate, PEG-55 propylene glycol oleate, PEG-150 distearate, and PEG-180/laureth-50/TMMG copolymer,
  (IV) from 0.15% to 1% by weight of sodium hydroxide as only neutralizing agent,
  (V) up to 5% by weight of at least one of PEG-20 stearate, PEG-40 stearate and PEG-100 stearate,
  (VI) from 0% to 10% by weight of at least one of steareth-2, laureth-4 and ceteth-3, and
  (VII) from 1.0% to 5.0% by weight of at least one of a pigment and a dye comprising at least one of coated mica particles, $TiO_2$ particles, $Fe_2O_3$ particles, zinc oxide-coated $SiO_2$ particles, iron pearlescent pigments prepared without the use of mica, and aluminum pearlescent pigments.

56. The composition of claim 55, wherein (III) comprises at least one of an acrylate/alkyl acrylate crosspolymer and an acrylate/vinyl isodecanoate crosspolymer.

57. The composition of claim 55, wherein (III) comprises at least one of acrylate/steareth-20 methacrylate copolymer, acrylate/steareth-20 itaconate copolymer, acrylate/steareth-50 acrylate copolymer, acrylate/palmeth-25 acrylate copolymer and steareth-10 allyl ether/acrylate copolymer.

58. The composition of claim 55, wherein (III) comprises at least one of PEG-120 methylglucose dioleate, PEG-60 sorbitan tetraoleate, PEG-150 pentaerythrityl tetra-stearate, PEG-55 propylene glycol oleate, PEG-150 distearate and PEG-180/laureth-50/TMMG copolymer.

59. The composition of claim 55, wherein (III) comprises at least one of dimethicone/vinyl dimethicone crosspolymer and polysilicone-11.

60. The composition of claim 55, wherein (VI) comprises laureth-4.

* * * * *